United States Patent
Vitiello et al.

(10) Patent No.: US 6,322,789 B1
(45) Date of Patent: *Nov. 27, 2001

(54) HLA-RESTRICTED HEPATITIS B VIRUS CTL EPITOPES

(75) Inventors: Maria A. Vitiello, La Jolla; Robert W. Chesnut, Cardiff by the Sea, both of CA (US)

(73) Assignee: Epimmune, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/464,496

(22) Filed: Jun. 5, 1995

Related U.S. Application Data

(60) Division of application No. 07/935,811, filed on Aug. 26, 1992, now abandoned, which is a continuation-in-part of application No. 07/874,491, filed on Apr. 27, 1992, now abandoned, which is a continuation-in-part of application No. 07/827,682, filed on Jan. 29, 1992, now abandoned, which is a continuation-in-part of application No. 07/749,568, filed on Aug. 26, 1991, now abandoned.

(51) Int. Cl.$^7$ .................................................. A61K 39/29
(52) U.S. Cl. .................................... 424/189.1; 424/193.1; 424/196.11; 424/227.1
(58) Field of Search .............................. 424/184.1, 185.1, 424/189.1, 225.1, 227.1, 193.1, 196.11; 514/2, 13; 530/300, 326, 350, 826; 930/223

(56) References Cited

U.S. PATENT DOCUMENTS

| | | | |
|---|---|---|---|
| 4,235,877 | 11/1980 | Fullerton | 424/450 |
| 4,428,941 | 1/1984 | Galibert et al. | 514/2 |
| 4,487,715 | 12/1984 | Nitecki et al. | 530/334 |
| 4,599,230 | 7/1986 | Milich et al. | 424/189.1 |
| 4,599,231 | 7/1986 | Milich et al. | 424/189.1 |
| 4,818,527 * | 4/1989 | Thornton et al. | 424/88 |
| 4,837,028 | 6/1989 | Allen | 424/1.21 |
| 4,882,145 | 11/1989 | Thornton et al. | 424/189.1 |
| 4,900,547 | 2/1990 | Levy et al. | 424/85.1 |
| 4,935,235 | 6/1990 | Rutter et al. | 424/189.1 |
| 5,013,548 | 5/1991 | Haynes et al. | . |
| 5,017,558 | 5/1991 | Vyas | 424/189.1 |
| 5,019,386 | 5/1991 | Machida et al. | 424/189.1 |
| 5,039,522 | 8/1991 | Neurath | 424/194.1 |
| 5,128,319 | 7/1992 | Arlinghaus | . |

FOREIGN PATENT DOCUMENTS

| | | |
|---|---|---|
| 105481 | 4/1984 | (EP) . |
| 171908 | 2/1986 | (EP) . |
| 271302 | 6/1988 | (EP) . |
| 429816 | 6/1991 | (EP) . |
| 431327 | 6/1991 | (EP) . |
| 433242 | 6/1991 | (EP) . |
| 60-161999 | 8/1985 | (JP) . |
| WO 91 09869 A | 7/1991 | (WO) . |
| 93/03764 | 3/1993 | (WO) . |
| WO 93/03764 | 3/1993 | (WO) . |

WO 81/00577 * 3/1981 (WO) ............................. C12N/15/00

OTHER PUBLICATIONS

Rehermann et al., "The Cytotoxic T Lymphocyte Response to Multiple Hepatitis B Virus Polymerase Epitopes During and After Acute Viral Hepatitis", (J. Exp. Med. 181, 1047–1058 (1995).*

Hilleman, "Comparative Biology and Pathogenesis of AIDS and Hepatitis B Viruses: Related but Different", AIDS Res. Hum. Retrovir. 10, 1409–1419 (1994).*

Bowie et al., "Deciphering the Message in Protein Sequences: Tolerance to Amino Acid Substitutions", Science 247, 1306–1310 (1990).*

Kumar et al., "Amino acid variations at a single residue in an automimmune peptide profoundly affect its properties:", Proc. Natl. Acad. Sci. USA 87, 1337–1341 (1990).*

Lewin, "When Does Homology Mean Something Else?", Science 237, 1570 (1987).*

Reeck et al., "'Homology' in Proteins and Nucleic Acids: A Terminology Muddle and a Way out It", Cell 50, 667 (1987).*

Falk et al., "Allele–specific motifs revealed by sequencing of self–peptides eluted from MHC molecules", Nature 351, 290–296 (May 1991).*

Carbone et al., "Induction of Cytotoxic T Cells by Primary in vitro Stimulation with Peptides", J. Exp. Med., 167, 1767–1779 (1988).*

Ferrari et al., "Identification of Immunodominant T Cell Epitopes of the Hepatitis B Virus Nucleocapsid Antigen", J. Clin. Invest. 88, 214–222 (1991).*

Francis, et al., "Non–responsiveness to a foot–and–mouth disease virus peptide overcome by addition of foreign helper T–cell determinants"; *Nature*, vol. 330, pp. 168–170 (Nov. 1987).

(List continued on next page.)

*Primary Examiner*—Donna Wortman
(74) *Attorney, Agent, or Firm*—Morrison & Foerster LLP

(57) ABSTRACT

Cytotoxic T lymphocyte-stimulating peptides induce HLA-restricted responses to hepatitis B virus antigens. The peptides, derived from CTL epitopic regions of both HBV surface and nucleocapsid antigens, are particularly useful in the treatment and prevention of HBV infection, including the treatment of chronically infected HBV carriers. The peptides can be formulated as HBV vaccines and pharmaceutical compositions, such as lipid-containing compositions for enhancing the HLA-restricted CTL responses. The peptides are also useful in diagnostic methods, such as predicting which HBV-infected individuals are prone to developing chronic infection.

22 Claims, 18 Drawing Sheets

OTHER PUBLICATIONS

Jolivet, et al., "Polyvalent synthetic vaccines: relationship between T epitopes and immunogenicity"; *Vaccine,* vol. 8, pp. 35–40 (Feb. 1990).

Sette, et al. "The Relationship Between Class I Binding Affinity and Immunogenicity of Potential Cytotoxic T Cell Epitopes"; *The Journal of Immunology* pp. 5586–5592 (1994).

Wakita, et al., "Gamma–Interferon Production in Response to Hepatitis B Core Protein and Its Synthetic Peptides in Patients with Chronic Hepatitis B Virus Infrection"; *Digestion,* vol. 47, pp 149–155, (1990).

Yewdell, et al, "Immunodominance in Major Histocompatibility Complex Class I–Restricted T Lymphocyte Response"; *Annu. Rev. Immunol.* vol. 17, pp 51–88, (1999).

Zinkernagel et al., "The Lymphoreticular System in Triggering Virus Plus Self–Specific Cytotoxic T Cells: Evidence for T Help", *J. Exp. Med.,* 147:897–911 (1978).

von Boehmer et al., "Distinct Ir Genes for Helper and Killer Cells in the Cytotoxic Response to H–Y Antigen", *J. Exp. Med.,* 150:1134–1142 (Nov., 1979).

Melief et al., "Cooperation Between Subclasses of T Lymphocytes in the in vitro Generation of Cytotoxicity Against a Mutant H–2K Difference An Analysis with Anti–Lyt Antisera", *Eur. J. Immunol.* 9:7–12 (1979).

Pasek et al., *Nature,* 282:575–579 (1979).

Lerner et al., "Chemically Synthesized Peptides Predicted form the Nucleotide Sequence of the Hepatitis B Virus Genome Elicit Antibodies Reactive with the Native Envelope Protein of Dane Particles", *Proc. Natl. Acad. Sci. USA* 78:3403–3407 (Jun., 1981).

Widmer et al., "Antigen–Driven Helper Cell–independent Cloned Cytolytic T Lymphocytes", *Nature* 294:750–752 (1981).

Bhatnagar et al., "Immune Response to Synthetic Peptide Analogues of Hepatitis B Surface Antigen Specific for the Determinant", *Proc. Natl. Acad. Sci. USA* 79:4400–44–4 (Jul., 1982).

Mondelli et al., "Specificity of T Lymphocyte Cytotoxicity to Autologous Hepatocytes in Chronic Hepatitis B Virus Infection: Evidence that t Cells are Directed Against HBV Core Antigen Expressed on Hepatocytes", *J. Immunol.,* 129:2773–2778 (Dec., 1982).

Lamb et al., "Human T–Cell Clones Recognize Chemically Synthesized Peptides of Influenza Haemagglutinin," *Nature,* 300:566–569 (1982).

von Boehmer et al., "Autonomously Proliferating K/D–restricted Cytolytic T Cell Clones", *Eur. J. Immunol.* 13:176–179 (1983).

Neurath et al., "Specificity of Antibodies Elicited by a Synthetic Peptide having a Sequence in Common with a Fragment of a Virus Protein—The Hepatitis B Surface Antigen", *Develop. Biol. Standard,* 54:103–112 (1983).

von Boehmer et al., "Lyt–2 T Cell–Independent Functions of Lyt-2$^+$ Cells Stimulated with Antigen or Concanavalin A", *J. Immunol.,* 133:59–64 (Jul., 1984).

Milich et al., "Immunogenetics and Cellular Correlates of the Immune Response to Hepatitis B Surface Antigen Determinants", *Adv. Hepatitis Res.* Masson, NY, NY USA 91–109 (1984).

Hopp, "Immunogenicity of a synthetic HBsAg Peptide: Enhancement by Conjugate to a Fatty Acid Carrier", *Molecular Immunol.* 21:13–16 (1984).

Munekata (ed.) "Peptide Chemistry 1983" published 1984 by Protein Research Foundation (OSAKA), pp. 215–220.

Sprent et al., "Properties of Purified T Cell Subsets", *J. Exp. Med.,* 162:2068–2088 (Dec., 1985).

Bessler et al., "The Synthetic Analog of Bacterial Lipoprotein are Potent Immunoadjuvants in Combination with or Covalently Linked to Antigen", *Prog. Leukocyte Biol.* 5:337–344 (1986).

Lamb et al., "Influence of Antigen Structure on the Activation and Induction of Unresponsiveness in Cloned Human T Lymphocytes," *Immunology* 57:331–335 (1986).

Watari et al., "A Synthetic Peptide Induces Long–Term Protection from Lethal Infection with Herpes Simplex Virus 2", *J. Exp. Med.,* 165:459–470 (Feb., 1987).

Gotch et al., "Cytotoxic T Lymphocytes Recognize a Fragment of Influenza Virus Matrix Protein in Associate with HLA–A2", *Nature* 326:881–882 (Apr. 30, 1987).

Buller et al., "Induction of Cytotoxic T–Cell Responses in vivo in the Absence of CD4 Helper Cells", *Nature* 328:76–79 (Jul. 2, 1987).

Milich et al., "Immune Response to Hepatitis B Virus Core Antigen (HBcAg): Localization of T Cell Recognition Sites Within HBcAg/HBeAg", *J. Immunol.,* 139:1223–1231 (1987).

Staerz U. et al., "Cytotoxic T Lymphocytes Against a Soluble Protein," *Nature,* 329:449–451 (Oct. 1, 1987).

Milich et al., "Antibody Production to the Nucleocapsid and Envelope of the Hepatitis B Virus Primed by a Single Synthetic T Cell Site", *Nature* 329:547–549 (1987).

Mondelli et al., "Definition of Hepatitis B Virus (HBV)–specific Target Antigens Recognized by Cytotoxic T Cells in Acute HBV Infection", *Clin. Exp. Immunol.,* 63:242–250 (1987).

Milich et al., "Hepatitis B Synthetic Immunogen Comprised of Nucleocapsid T–cell Sites and an Envelope B–cell Epitope", *Proc. Natl. Acad. Sci. USA* 85:1610–1614 (Mar., 1988).

Celis et al., "Recognition of Hepatitis B Surface Antigen by Human T Lymphocytes" *J. Immunol.* 140:1808–1815 (1988).

Carbone et al., "Induction of Cytotoxic T Lymphocytes by Primary in vitro Stimulation with Peptides", *J. Exp. Med.,* 167:1767–1779 (Jun., 1988).

Moore et al., "Introduction of Soluble Protein into the Class I Pathway of Antigen Processing and Presentation", *Cell* 54:777–785 (Sep. 9, 1988).

Milich et al., "Comparative Immunogenicity of Hepatitis B Virus Core and E Antigens", *J. Immunol.* 141:3617–3624 (1988).

Gotch et al., "Recognition of Influenza A Matrix Protein by HLA–A2–Restricted Cytotoxic T Lymphocytes", *J. Exp. Med.* 163:2045–2057 (Dec., 1988).

Milich, "T– and B–cell Recognition of Hepatitis B Viral Antigens", *Immunol. Today* 9:380–386 (1988).

Hayashi et al., "Studies on Peptides CLXVI. Solid–Phase Synthesis and Immunological Properties of Fragment Peptides Related to Human Hepatitis B virus Surface Antigen (HBsAg) and Its Pre–S2 Gene" *Chem. Pharm. Bull.* 36(12):4993–4994 (1988).

Claverie et al., "T–Immunogenic Peptides are Constituted of Rare Sequence Patterns. Use in the Identification of T Epitopes in the Human Immunodeficiency Virus gag Protein," *Eur. J. Immunol.* 18:1547–53 (1988).

Brown et al., "Genetic Control and Fine Specificity of the Immune Response to a Synthetic Peptide of Influenza Virus Hemagglutinin," *J. Virol.,* 62:1746–52 (1988).

Braciale et al., "Class I Major Histocompatibility Complex-restricted Cytolytic T Lymphocytes Recognize a Limited Number of sites on the Influenza Hemagglutinin", *Proc. Natl. Acad. Sci. USA* 86:277–281 (Jan., 1989).

Reitermann et al., "Lipopeptide Derivatives of Bacterial Lipoprotein Constitute Potent Immune Adjuvants Combined with or Covalently Coupled to Antigen or Hapten", *Biol. Chem.* 370:343–352 (Apr., 1989).

Ishioka et al., "Induction of Class I MHC–restricted, Peptide–specific Cytolytic T Lymphocytes by Peptide Priming in vivo", *J. Immunol.,* 143:1094–1100 (Aug. 15, 1989).

Klavinskis et al., "Molecularly Engineered Vaccine Which Expresses an Immunodominant T–cell Epitope Induces Cytotoxic T Lymphocytes that Confer Protection for Lethal Virus Infection," *J. Virol.,* 63:4311–4316 (Oct., 1989).

Bevan, "Stimulating Killer Cells", *Nature* 342:478–479 (Nov. 30, 1989).

Deres et al., "In vivo Priming of Virus–Specific Cytotoxic T Lymphocytes with Synthetic Lipopeptide Vaccine", *Nature* 342:561–564 (Nov. 30, 1989).

Tam et al., "Vaccine Engineering: Enhancement of Immunogenicity of Synthetic Peptide Vaccines Related to Hepatitis in Chemically Defined Models Consisting of T– and B–cell Epitopes", *Proc. Natl. Acad. Sci. USA* 86:9084–9088 (Dec., 1989).

Kuroda et al., "Efficient Expression of Genetically Engineered Hepatitis B Virus Surface Antigen P31 Proteins in Yeast," *Gene,* 78:297–308 (1989).

Moriyama et al., "Immunobiology and Pathogenesis of Hepatocellular Injury in Hepatitis B Virus Transgenic Mice", *Science* 248:361–364 (Apr. 20, 1990).

Aichele et al., "Antiviral Cytotoxic T Cell Response Induced by in vivo Priming with a Free Synthetic Peptide", *J. Exp. Med.,* 171:1815–1820 (May, 1990).

Aggarwal et al., "Oral Salmonella: Malaria Circumsporozoite Recombinants Induce Specific $CD8^+$ Cytotoxic T Cells", *J. Exp. Med.,* 172:1083–1090 (Oct., 1990).

Van Bleek et al., "Isolation of an Endogenously Processed Immunodominant Viral Peptide from the Class $IH-2K^b$ Molecule", *Nature* 348:213–216 (Nov. 15, 1990).

Rotzschke et al., "Isolation and Analysis of Naturally Processed Viral Peptides as Recognized by Cytotoxic T cells", *Nature* 348:252–254 (Nov. 15, 1990).

Golvano et al., "Polarity of Immunogens: Implications for Vaccine Design", *Eur. J. Immunol.* 20:2363–2366 (1990).

Ishioka et al., "Class I MHC–restricted, Peptide–specific Cytotoxic T Lymphocytes Generated by Peptide Priming in vivo", *Vaccines 90,* Cold Spring Harbor Press, pp. 7–11 (1990).

Wakita et al., "Gamma–Interferon Production in Response to Hepatitis B Core Protein and Its Synthetic Peptides in Patients with Chronic Hepatitis B Virus Infection," *Digestion,* 47:149–55 (1990).

Kast et al., "Protection Against Lethal Sendai Virus Infection by in vivo Priming of Virus–specific Cytotoxic T Lymphocytes with a Free Synthetic Peptide", *Proc. Natl. Acad. Sci. USA* 88:2283–2287 (Mar., 1991).

Schumacher et al., "Peptide Selection by MHC Class I Molecules", *Nature* 350:703–706 (Apr. 25, 1991).

Falk et al., "Allele–specific Motifs Revealed by Sequencing of Self–peptides Eluted from MHC Molecules", *Nature* 351:290–296 (May 23, 1991).

Ferrari et al., "Identification of Immunodominant T Cell Epitopes of the Hepatitis B Virus Nucleocapsid Antigen", *J. Clin. Invest.,* 88:214–222 (Jul., 1991).

Widmann, C. et al., "Differential Stability of Antigenic MHC Class I–Restricted Synthetic Peptides," *J. Immunol.,* 147:3745–3751 (1991).

Fayolle, C. et al., "In Vivo Induction of Cytotoxic T Cell Response by a Free Synthetic Peptide Requires CD4+ T Cell Help," *J. Immunol.,* 147:4069–4073 (Dec. 15, 1991).

Penna et al., "Cytotoxic T Lymphocytes Recognize an HLA–A2–Restricted Epitope within the Hepatitis B Virus Nucleocapsid Antigen", *J. Exp. Med.,* 174:1565–1570 (Dec., 1991).

Sarobe et al., "Induction of Antibodies Against a Peptide Hapten Does Not Require Covalent Linkage Between the Hapten and a Class II Presentable T Helper Peptide", *Eur. J. Immunol.* 21:1555–1558 (1991).

Wiesmuller, et al., "Lipopeptide–Helper T–Cell Epitope–CTL Epitope Conjugate Induces Antibodies Against the CTL Epitope", *Innovation Perspect. Solid–Phase Synth. Collect. Papers,* Int. Symp. 2nd 1991, pp. 499–502, (1991).

Cassell et al., "Linked Recognition of Helper and Cytotoxic Antigenic Determinants for the Generation of Cytotoxic T Lymphocytes", *Ann N.Y. Acad. Sci.,* pp. 51–60 (1991).

Sallberg et al., "Human and Murine B–Cells Recognized the HBeAg/BETA (or HBe2) Epitope as a Linear Determinant," *Mol. Immunol.* 28:716–726 (1991).

Romera, P. et al., "Immunization with Synthetic Peptides Containing a Defined Malaria Epitope Induces a Highly Diverse Cytotoxic T Lymphocyte Response," *J. Immunol.,* 148:1871–1878 (Mar. 15, 1992).

Martinon, F. et al., "Immunization of Mice with Lipopeptides Bypasses the Prerequisite for Adjuvant," *J. Immunol.,* 149:3416–3422 (1992).

Lasarte, J. et al., "Induction of Cytotoxic T Lymphocytes in Mice Against the Principal Neutralizing Domain of HIV–1 by Immunization with an Engineered T–Cytotoxic–T–Helper Synthetic Peptide Construct," *Cellular Immunol.* 141:211–218 (1992).

Widmann et al., "T Helper Epitopes Enhance the Cytotoxic Response of Mice Immunized with MHC Class I–Restricted Malaria Peptides," *J. Immunol. Meth.,* 155:95–99 (1992).

Newton–Nash et al., "Effects of Localized HLA Class II β Chain Polymorphism on Binding of Antigenic Peptide and Stimulation of T Cells," *Human Immunol.,* 33:213–222 (1992).

Kumar et al., "'Universal' T Helper Cell Determinants Enhance Immunogenicity of a *Plasmodium Falciparum* Merozoite Surface Antigen Peptide," *J. Immunol.* 148:1499–1505 (1992).

\* cited by examiner

SEQUENCE LISTING

<160> NUMBER OF SEQ ID NOS: 75

<210> SEQ ID NO 1
<211> LENGTH: 20
<212> TYPE: PRT
<213> ORGANISM: HBV surface antigen

<400> SEQUENCE: 1

Asn Cys Thr Cys Ile Pro Ile Pro Ser Ser Trp Ala Phe Gly Lys Phe
1               5                   10                  15

Leu Trp Glu Trp
            20

<210> SEQ ID NO 2
<211> LENGTH: 20
<212> TYPE: PRT
<213> ORGANISM: HBV surface antigen

<400> SEQUENCE: 2

Leu Ser Pro Thr Val Trp Leu Ser Val Ile Trp Met Met Trp Tyr Trp
1               5                   10                  15

Gly Pro Ser Leu
            20

<210> SEQ ID NO 3
<211> LENGTH: 10
<212> TYPE: PRT
<213> ORGANISM: HBV surface antigen

<400> SEQUENCE: 3

Leu Ser Pro Thr Val Trp Leu Ser Val Ile
1               5                   10

<210> SEQ ID NO 4
<211> LENGTH: 20
<212> TYPE: PRT
<213> ORGANISM: HBV surface antigen

<400> SEQUENCE: 4

Thr Asn Met Gly Leu Lys Phe Arg Gln Leu Leu Trp Phe His Ile Ser
1               5                   10                  15

Cys Leu Thr Phe
            20

<210> SEQ ID NO 5
<211> LENGTH: 12
<212> TYPE: PRT
<213> ORGANISM: HBV surface antigen

<400> SEQUENCE: 5

Ala Ser Asn Met Gly Leu Lys Phe Arg Gln Leu Leu
1               5                   10

<210> SEQ ID NO 6
<211> LENGTH: 10
<212> TYPE: PRT
<213> ORGANISM: HBV surface antigen

<400> SEQUENCE: 6

Met Gly Leu Lys Phe Arg Gln Leu Leu Trp
1               5                   10

```
<210> SEQ ID NO 7
<211> LENGTH: 20
<212> TYPE: PRT
<213> ORGANISM: HBV surface antigen

<400> SEQUENCE: 7

Ala Ser Ala Arg Phe Ser Trp Leu Ser Leu Leu Val Pro Phe Val Gln
 1               5                  10                  15

Trp Phe Val Gly
            20

<210> SEQ ID NO 8
<211> LENGTH: 9
<212> TYPE: PRT
<213> ORGANISM: HBV surface antigen

<400> SEQUENCE: 8

Trp Leu Ser Leu Leu Val Pro Phe Val
 1               5

<210> SEQ ID NO 9
<211> LENGTH: 9
<212> TYPE: PRT
<213> ORGANISM: HBV surface antigen

<400> SEQUENCE: 9

Asn Met Gly Leu Lys Phe Arg Gln Leu
 1               5

<210> SEQ ID NO 10
<211> LENGTH: 20
<212> TYPE: PRT
<213> ORGANISM: HBV HBC 1-20

<400> SEQUENCE: 10

Met Asp Ile Asp Pro Tyr Lys Glu Phe Gly Ala Thr Val Glu Leu Leu
 1               5                  10                  15

Ser Phe Leu Pro
            20

<210> SEQ ID NO 11
<211> LENGTH: 20
<212> TYPE: PRT
<213> ORGANISM: HBV HBC 50-69

<400> SEQUENCE: 11

Pro His His Tyr Ala Leu Arg Gln Ala Ile Leu Cys Trp Gly Glu Leu
 1               5                  10                  15

Met Tyr Leu Ala
            20

<210> SEQ ID NO 12
<211> LENGTH: 20
<212> TYPE: PRT
<213> ORGANISM: HBV HBC 100-119

<400> SEQUENCE: 12

Leu Leu Trp Phe His Ile Ser Cys Leu Thr Phe Gly Arg Glu Thr Val
 1               5                  10                  15

Ile Glu Tyr Leu
            20
```

<210> SEQ ID NO 13
<211> LENGTH: 15
<212> TYPE: PRT
<213> ORGANISM: HBV HBC 117-131

<400> SEQUENCE: 13

Glu Tyr Leu Val Ser Phe Gly Val Trp Ile Arg Thr Pro Pro Ala
 1               5                  10                  15

<210> SEQ ID NO 14
<211> LENGTH: 20
<212> TYPE: PRT
<213> ORGANISM: HBV  HBC 120-139

<400> SEQUENCE: 14

Val Ser Phe Gly Val Trp Ile Arg Thr Pro Pro Ala Tyr Arg Pro Pro
 1               5                  10                  15

Asn Ala Pro Ile
            20

<210> SEQ ID NO 15
<211> LENGTH: 14
<212> TYPE: PRT
<213> ORGANISM: Tetanus toxoid 830-843

<400> SEQUENCE: 15

Gln Tyr Ile Lys Ala Asn Ser Lys Phe Ile Gly Ile Thr Glu
 1               5                  10

<210> SEQ ID NO 16
<211> LENGTH: 17
<212> TYPE: PRT
<213> ORGANISM: Malaria circumsporozoite 382-298

<400> SEQUENCE: 16

Lys Ile Ala Lys Met Glu Lys Ala Ser Ser Val Phe Asn Val Val Asn
 1               5                  10                  15

Ser

<210> SEQ ID NO 17
<211> LENGTH: 21
<212> TYPE: PRT
<213> ORGANISM: Malaria circumsporozoite 378-398

<400> SEQUENCE: 17

Asp Ile Glu Lys Lys Ile Ala Lys Met Glu Lys Ala Ser Ser Val Phe
 1               5                  10                  15

Asn Val Val Asn Ser
            20

<210> SEQ ID NO 18
<211> LENGTH: 13
<212> TYPE: PRT
<213> ORGANISM: Influenza epitope 307-319

<400> SEQUENCE: 18

Pro Lys Tyr Val Lys Gln Asn Thr Leu Lys Leu Ala Thr
 1               5                  10

<210> SEQ ID NO 19
<211> LENGTH: 13
<212> TYPE: PRT
<213> ORGANISM: Artificial Sequence
<220> FEATURE:

<223> OTHER INFORMATION: T helper epitope HBC 128-140

<400> SEQUENCE: 19

Thr Pro Pro Ala Tyr Arg Pro Pro Asn Ala Pro Ile Leu
1               5                   10

<210> SEQ ID NO 20
<211> LENGTH: 23
<212> TYPE: PRT
<213> ORGANISM: Artificial Sequence
<220> FEATURE:
<223> OTHER INFORMATION: T helper epitope HBC 128-140

<400> SEQUENCE: 20

Thr Pro Pro Ala Tyr Arg Pro Pro Asn Ala Pro Ile Leu Phe Leu Pro
1               5                   10                  15

Ser Asp Phe Phe Pro Ser Val
            20

<210> SEQ ID NO 21
<211> LENGTH: 26
<212> TYPE: PRT
<213> ORGANISM: Artificial Sequence
<220> FEATURE:
<223> OTHER INFORMATION: T helper epitope HBC 128-140

<400> SEQUENCE: 21

Thr Pro Pro Ala Tyr Arg Pro Pro Asn Ala Pro Ile Leu Ala Ala Ala
1               5                   10                  15

Phe Leu Pro Ser Asp Phe Phe Pro Ser Val
            20                  25

<210> SEQ ID NO 22
<211> LENGTH: 10
<212> TYPE: PRT
<213> ORGANISM: Artificial Sequence
<220> FEATURE:
<223> OTHER INFORMATION: HBenv 360-368

<400> SEQUENCE: 22

Trp Met Met Trp Tyr Trp Gly Pro Ser Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Oligopeptide

<400> SEQUENCE: 23

Phe Leu Pro Ser Asp Phe Phe Pro Ser Val
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Oligopeptide

<400> SEQUENCE: 24

Lys Ser Ser Phe Leu Pro Ser Asp Phe Phe Pro Ser Val
1               5                   10

<210> SEQ ID NO 25
<211> LENGTH: 24
<212> TYPE: PRT
<213> ORGANISM: Artificial sequence
<220> FEATURE:
<223> OTHER INFORMATION: Oligopeptide

<400> SEQUENCE: 25

Gln Tyr Ile Lys Ala Asn Ser Lys Phe Ile Gly Ile Thr Glu Phe Leu
 1               5                  10                  15

Pro Ser Asp Phe Phe Pro Ser Val
            20

<210> SEQ ID NO 26
<211> LENGTH: 27
<212> TYPE: PRT
<213> ORGANISM: Artificial Sequence
<220> FEATURE:
<223> OTHER INFORMATION: Oligopeptide

<400> SEQUENCE: 26

Gln Tyr Ile Lys Ala Asn Ser Lys Phe Ile Gly Ile Thr Glu Ala Ala
 1               5                  10                  15

Ala Phe Leu Pro Ser Asp Phe Phe Pro Ser Val
            20                  25

<210> SEQ ID NO 27
<211> LENGTH: 28
<212> TYPE: PRT
<213> ORGANISM: Artificial Sequence
<220> FEATURE:
<223> OTHER INFORMATION: Oligopeptide

<400> SEQUENCE: 27

Gln Thr Tyr Ile Lys Ala Asn Ser Lys Phe Ile Gly Ile Thr Glu Ala
 1               5                  10                  15

Ala Ala Phe Leu Pro Ser Asp Phe Phe Pro Ser Val
            20                  25

<210> SEQ ID NO 28
<211> LENGTH: 28
<212> TYPE: PRT
<213> ORGANISM: Artificial Sequence
<220> FEATURE:
<223> OTHER INFORMATION: Oligopeptide

<400> SEQUENCE: 28

Gln Thr Tyr Ile Lys Ala Asn Ser Lys Phe Ile Gly Ile Thr Glu Ala
 1               5                  10                  15

Ala Ala Phe Leu Pro Ser Asp Phe Phe Pro Ser Val
            20                  25

<210> SEQ ID NO 29
<211> LENGTH: 30
<212> TYPE: PRT
<213> ORGANISM: Artificial Sequence
<220> FEATURE:
<223> OTHER INFORMATION: Oligopeptide

<400> SEQUENCE: 29

Lys Ser Ser Gln Tyr Ile Lys Ala Asn Ser Lys Phe Ile Gly Ile Thr
 1               5                  10                  15

Glu Ala Ala Ala Phe Leu Pro Ser Asp Phe Phe Pro Ser Val
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Oligopeptide

<400> SEQUENCE: 30

Gln Tyr Ile Lys Ala Asn Ser Lys Phe Ile Gly Ile Thr Glu
 1               5                  10

<210> SEQ ID NO 31
<211> LENGTH: 24
<212> TYPE: PRT
<213> ORGANISM: Artificial Sequence
<220> FEATURE:
<223> OTHER INFORMATION: Oligopeptide

<400> SEQUENCE: 31

Phe Leu Pro Ser Asp Phe Phe Pro Ser Val Gln Tyr Ile Lys Ala Asn
 1               5                  10                  15

Ser Lys Phe Ile Gly Ile Thr Glu
            20

<210> SEQ ID NO 32
<211> LENGTH: 27
<212> TYPE: PRT
<213> ORGANISM: Artificial Sequence
<220> FEATURE:
<223> OTHER INFORMATION: Oligopeptide

<400> SEQUENCE: 32

Lys Ser Ser Gln Tyr Ile Lys Ala Asn Ser Lys Phe Ile Gly Ile Thr
 1               5                  10                  15

Glu Phe Leu Pro Ser Asp Phe Pro Ser Val
            20                  25

<210> SEQ ID NO 33
<211> LENGTH: 10
<212> TYPE: PRT
<213> ORGANISM: Artificial Sequence
<220> FEATURE:
<223> OTHER INFORMATION: HBenv 332-341

<400> SEQUENCE: 33

Arg Phe Ser Trp Leu Ser Leu Leu Val Pro
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: peptide 923.15

<400> SEQUENCE: 34

Leu Leu Val Pro Phe Val Gln Trp Phe Val
 1               5                  10

<210> SEQ ID NO 35
<211> LENGTH: 14
<212> TYPE: PRT
<213> ORGANISM: Ovalbumin 323-336

<400> SEQUENCE: 35

Ile Ser Gln Ala Val His Ala Ala His Ala Glu Ile Asn Glu
1               5                   10

<210> SEQ ID NO 36
<211> LENGTH: 29
<212> TYPE: PRT
<213> ORGANISM: Artificial Sequence
<220> FEATURE:
<223> OTHER INFORMATION: Oligopeptide

<400> SEQUENCE: 36

Ala Cys Gln Tyr Ile Lys Ala Asn Ser Lys Phe Ile Gly Ile Thr Glu
1               5                   10                  15

Ala Ala Ala Phe Leu Pro Ser Asp Phe Phe Pro Ser Val
            20                  25

<210> SEQ ID NO 37
<211> LENGTH: 9
<212> TYPE: PRT
<213> ORGANISM: Flu NP 147-155

<400> SEQUENCE: 37

Thr Tyr Gln Arg Thr Arg Ala Leu Val
1               5

<210> SEQ ID NO 38
<211> LENGTH: 12
<212> TYPE: PRT
<213> ORGANISM: Artificial Sequence
<220> FEATURE:
<223> OTHER INFORMATION: 932.07 (PAM)2

<400> SEQUENCE: 38

Lys Ser Ser Thr Tyr Gln Arg Thr Arg Ala Leu Val
1               5                   10

<210> SEQ ID NO 39
<211> LENGTH: 23
<212> TYPE: PRT
<213> ORGANISM: Artificial Sequence
<220> FEATURE:
<223> OTHER INFORMATION: Oligopeptide

<400> SEQUENCE: 39

Thr Tyr Gln Arg Thr Arg Ala Leu Val Ile Ser Gln Ala Val His Ala
1               5                   10                  15

Ala His Ala Glu Ile Asn Glu
            20

<210> SEQ ID NO 40
<211> LENGTH: 26
<212> TYPE: PRT
<213> ORGANISM: Artificial Sequence
<220> FEATURE:
<223> OTHER INFORMATION: Oligopeptide

<400> SEQUENCE: 40

Lys Ser Ser Thr Tyr Gln Arg Thr Arg Ala Leu Val Ile Ser Gln Ala
1               5                   10                  15

Val His Ala Ala His Ala Glu Ile Asn Glu
            20                  25

<210> SEQ ID NO 41
<211> LENGTH: 23
<212> TYPE: PRT

―continued

```
<213> ORGANISM: Artificial Sequence
<220> FEATURE:
<223> OTHER INFORMATION: Oligopeptide

<400> SEQUENCE: 41

Ile Ser Gln Ala Val His Ala Ala His Ala Glu Ile Asn Glu Thr Tyr
1               5                   10                  15

Gln Arg Thr Arg Ala Leu Val
            20

<210> SEQ ID NO 42
<211> LENGTH: 26
<212> TYPE: PRT
<213> ORGANISM: Artificial Sequence
<220> FEATURE:
<223> OTHER INFORMATION: Oligopeptide

<400> SEQUENCE: 42

Lys Ser Ser Ile Ser Gln Ala Val His Ala Ala His Ala Glu Ile Asn
1               5                   10                  15

Glu Thr Tyr Gln Arg Thr Arg Ala Leu Val
            20                  25

<210> SEQ ID NO 43
<211> LENGTH: 26
<212> TYPE: PRT
<213> ORGANISM: Artificial Sequence
<220> FEATURE:
<223> OTHER INFORMATION: Oligopeptide

<400> SEQUENCE: 43

Ile Ser Gln Ala Val His Ala Ala His Ala Glu Ile Asn Glu Ala Ala
1               5                   10                  15

Ala Thr Tyr Gln Arg Thr Arg Ala Leu Val
            20                  25

<210> SEQ ID NO 44
<211> LENGTH: 29
<212> TYPE: PRT
<213> ORGANISM: Artificial Sequence
<220> FEATURE:
<223> OTHER INFORMATION: Oligopeptide

<400> SEQUENCE: 44

Lys Ser Ser Ile Ser Gln Ala Val His Ala Ala His Ala Glu Ile Asn
1               5                   10                  15

Glu Ala Ala Ala Thr Tyr Gln Arg Thr Arg Ala Leu Val
            20                  25

<210> SEQ ID NO 45
<211> LENGTH: 19
<212> TYPE: PRT
<213> ORGANISM: Artificial Sequence
<220> FEATURE:
<223> OTHER INFORMATION: 923.12

<400> SEQUENCE: 45

Ser Ala Arg Phe Ser Trp Leu Ser Leu Leu Val Pro Phe Val Gln Trp
1               5                   10                  15

Phe Val Gly

<210> SEQ ID NO 46
<211> LENGTH: 18
<212> TYPE: PRT
```

```
<213> ORGANISM: Artificial Sequence
<220> FEATURE:
<223> OTHER INFORMATION: 923.11

<400> SEQUENCE: 46

Ala Arg Phe Ser Trp Leu Ser Leu Leu Val Pro Phe Val Gln Trp Phe
1               5                   10                  15

Val Gly

<210> SEQ ID NO 47
<211> LENGTH: 17
<212> TYPE: PRT
<213> ORGANISM: Artificial Sequence
<220> FEATURE:
<223> OTHER INFORMATION: 923.10

<400> SEQUENCE: 47

Arg Phe Ser Trp Leu Ser Leu Leu Val Pro Phe Val Gln Trp Phe Val
1               5                   10                  15

Gly

<210> SEQ ID NO 48
<211> LENGTH: 16
<212> TYPE: PRT
<213> ORGANISM: Artificial Sequence
<220> FEATURE:
<223> OTHER INFORMATION: 923.09

<400> SEQUENCE: 48

Phe Ser Trp Leu Ser Leu Leu Val Pro Phe Val Gln Trp Phe Val Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: 923.08

<400> SEQUENCE: 49

Ser Trp Leu Ser Leu Leu Val Pro Phe Val Gln Trp Phe Val Gly
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: 923.07

<400> SEQUENCE: 50

Trp Leu Ser Leu Leu Val Pro Phe Val Gln Trp Phe Val Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: 923.06

<400> SEQUENCE: 51

Leu Ser Leu Leu Val Pro Phe Val Gln Trp Phe Val Gly
1               5                   10
```

```
<210> SEQ ID NO 52
<211> LENGTH: 12
<212> TYPE: PRT
<213> ORGANISM: Artificial Sequence
<220> FEATURE:
<223> OTHER INFORMATION: 923.05

<400> SEQUENCE: 52

Ser Leu Leu Val Pro Phe Val Gln Trp Phe Val Gly
 1               5                  10

<210> SEQ ID NO 53
<211> LENGTH: 11
<212> TYPE: PRT
<213> ORGANISM: Artificial Sequence
<220> FEATURE:
<223> OTHER INFORMATION: 923.04

<400> SEQUENCE: 53

Leu Leu Val Pro Phe Val Gln Trp Phe Val Gly
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: 923.03

<400> SEQUENCE: 54

Leu Val Pro Phe Val Gln Trp Phe Val Gly
 1               5                  10

<210> SEQ ID NO 55
<211> LENGTH: 9
<212> TYPE: PRT
<213> ORGANISM: Artificial Sequence
<220> FEATURE:
<223> OTHER INFORMATION: 923.02

<400> SEQUENCE: 55

Val Pro Phe Val Gln Trp Phe Val Gly
 1               5

<210> SEQ ID NO 56
<211> LENGTH: 8
<212> TYPE: PRT
<213> ORGANISM: Artificial Sequence
<220> FEATURE:
<223> OTHER INFORMATION: 923.01

<400> SEQUENCE: 56

Pro Phe Val Gln Trp Phe Val Gly
 1               5

<210> SEQ ID NO 57
<211> LENGTH: 9
<212> TYPE: PRT
<213> ORGANISM: Artificial Sequence
<220> FEATURE:
<223> OTHER INFORMATION: 923.34

<400> SEQUENCE: 57

Ala Ser Ala Arg Phe Ser Trp Leu Ser
 1               5

<210> SEQ ID NO 58
```

```
<211> LENGTH: 10
<212> TYPE: PRT
<213> ORGANISM: Artificial Sequence
<220> FEATURE:
<223> OTHER INFORMATION: 923.33

<400> SEQUENCE: 58

Ala Ser Ala Arg Phe Ser Trp Leu Ser Leu
 1               5                  10

<210> SEQ ID NO 59
<211> LENGTH: 9
<212> TYPE: PRT
<213> ORGANISM: Artificial Sequence
<220> FEATURE:
<223> OTHER INFORMATION: 923.32

<400> SEQUENCE: 59

Ser Ala Arg Phe Ser Trp Leu Ser Leu
 1               5

<210> SEQ ID NO 60
<211> LENGTH: 10
<212> TYPE: PRT
<213> ORGANISM: Artificial Sequence
<220> FEATURE:
<223> OTHER INFORMATION: 923.31

<400> SEQUENCE: 60

Ser Ala Arg Phe Ser Trp Leu Ser Leu Leu
 1               5                  10

<210> SEQ ID NO 61
<211> LENGTH: 9
<212> TYPE: PRT
<213> ORGANISM: Artificial Sequence
<220> FEATURE:
<223> OTHER INFORMATION: 923.30

<400> SEQUENCE: 61

Ala Arg Phe Ser Trp Leu Ser Leu Leu
 1               5

<210> SEQ ID NO 62
<211> LENGTH: 10
<212> TYPE: PRT
<213> ORGANISM: Artificial Sequence
<220> FEATURE:
<223> OTHER INFORMATION: 923.29

<400> SEQUENCE: 62

Ala Arg Phe Ser Trp Leu Ser Leu Leu Val
 1               5                  10

<210> SEQ ID NO 63
<211> LENGTH: 9
<212> TYPE: PRT
<213> ORGANISM: Artificial Sequence
<220> FEATURE:
<223> OTHER INFORMATION: 923.28

<400> SEQUENCE: 63

Arg Phe Ser Trp Leu Ser Leu Leu Val
 1               5

<210> SEQ ID NO 64
<211> LENGTH: 10
```

```
<212> TYPE: PRT
<213> ORGANISM: Artificial Sequence
<220> FEATURE:
<223> OTHER INFORMATION: 923.27

<400> SEQUENCE: 64

Arg Phe Ser Trp Leu Ser Leu Leu Val Pro
 1               5                   10

<210> SEQ ID NO 65
<211> LENGTH: 9
<212> TYPE: PRT
<213> ORGANISM: Artificial Sequence
<220> FEATURE:
<223> OTHER INFORMATION: 923.26

<400> SEQUENCE: 65

Phe Ser Trp Leu Ser Leu Leu Val Pro
 1               5

<210> SEQ ID NO 66
<211> LENGTH: 10
<212> TYPE: PRT
<213> ORGANISM: Artificial Sequence
<220> FEATURE:
<223> OTHER INFORMATION: 923.25

<400> SEQUENCE: 66

Phe Ser Trp Leu Ser Leu Leu Val Pro Phe
 1               5                   10

<210> SEQ ID NO 67
<211> LENGTH: 9
<212> TYPE: PRT
<213> ORGANISM: Artificial Sequence
<220> FEATURE:
<223> OTHER INFORMATION: 923.24

<400> SEQUENCE: 67

Ser Trp Leu Ser Leu Leu Val Pro Phe
 1               5

<210> SEQ ID NO 68
<211> LENGTH: 10
<212> TYPE: PRT
<213> ORGANISM: Artificial Sequence
<220> FEATURE:
<223> OTHER INFORMATION: 923.23

<400> SEQUENCE: 68

Ser Trp Leu Ser Leu Leu Val Pro Phe Val
 1               5                   10

<210> SEQ ID NO 69
<211> LENGTH: 10
<212> TYPE: PRT
<213> ORGANISM: Artificial Sequence
<220> FEATURE:
<223> OTHER INFORMATION: 923.21

<400> SEQUENCE: 69

Trp Leu Ser Leu Leu Val Pro Phe Val Gln
 1               5                   10

<210> SEQ ID NO 70
<211> LENGTH: 9
<212> TYPE: PRT
```

```
<213> ORGANISM: Artificial Sequence
<220> FEATURE:
<223> OTHER INFORMATION: 923.20

<400> SEQUENCE: 70

Leu Ser Leu Leu Val Pro Phe Val Gln
 1               5

<210> SEQ ID NO 71
<211> LENGTH: 10
<212> TYPE: PRT
<213> ORGANISM: Artificial Sequence
<220> FEATURE:
<223> OTHER INFORMATION: 923.19

<400> SEQUENCE: 71

Leu Ser Leu Leu Val Pro Phe Val Gln Trp
 1               5                  10

<210> SEQ ID NO 72
<211> LENGTH: 9
<212> TYPE: PRT
<213> ORGANISM: Artificial Sequence
<220> FEATURE:
<223> OTHER INFORMATION: 923.18

<400> SEQUENCE: 72

Ser Leu Leu Val Pro Phe Val Gln Trp
 1               5

<210> SEQ ID NO 73
<211> LENGTH: 10
<212> TYPE: PRT
<213> ORGANISM: Artificial Sequence
<220> FEATURE:
<223> OTHER INFORMATION: 923.17

<400> SEQUENCE: 73

Ser Leu Leu Val Pro Phe Val Gln Trp Phe
 1               5                  10

<210> SEQ ID NO 74
<211> LENGTH: 9
<212> TYPE: PRT
<213> ORGANISM: Artificial Sequence
<220> FEATURE:
<223> OTHER INFORMATION: 923.16

<400> SEQUENCE: 74

Leu Leu Val Pro Phe Val Gln Trp Phe
 1               5

<210> SEQ ID NO 75
<211> LENGTH: 9
<212> TYPE: PRT
<213> ORGANISM: Artificial Sequence
<220> FEATURE:
<223> OTHER INFORMATION: 923.14

<400> SEQUENCE: 75

Leu Val Pro Phe Val Gln Trp Phe Val
 1               5
```

HLA-RESTRICTED HEPATITIS B VIRUS CTL EPITOPES

RELATED APPLICATIONS

This application is a divisional of Ser. No. 07/935,811, filed Aug. 26, 1992, abandoned, which is a continuation-in-part of Ser. No. 07/874,491, filed Apr. 27, 1992, abandoned, which is a continuation-in-part of Ser. No. 07/827,682, filed Jan. 29, 1992, abandoned, which is a continuation-in-part of Ser. No. 07/749,568, abandoned, filed Aug. 26, 1991, each of which are incorporated herein by reference.

The invention may have been made with government support under a contract awarded by the National Institutes of Health and/or the National Institute of Allergy and Infectious Disease. Therefore, the government may have certain rights in the invention.

BACKGROUND OF THE INVENTION

The hepatitis B virus (HBV) is not believed to be directly responsible for damage to hepatocytes, despite its predilection for infecting such cells. Rather, non-viral host factors are implicated in the pathogenesis of hepatitis. It is suspected that a variation in immune responsiveness to HBV infection may account for the wide diversity of syndromes associated with HBV infection.

Following an acute HBV infection, approximately 90% of affected adults recover without sequelae and develop immunity to the virus, although the clinical course of the infection during the acute phase can itself be quite variable. In 5–10% of infected adults, a chronic HBV infection becomes established. Chronic HBV infection can range from asymptomatic carrier state to continuous hepatocellular necrosis and inflammation, and in some instances may lead to hepatocellular carcinoma. Children exposed to HBV infection, particularly those less than one year old, often develop chronic infection and represent the major source of chronic infection. Worldwide, nearly 200 million people are chronically infected with HBV. And finally, in a small percentage of HBV infections (0.1–0.5%) a fulminant hepatitis results in such extreme cell death in the liver that fewer than one-fifth to one-third of these patients survive.

The immune response to hepatitis B virus is as complex as the disease. A variety of humoral and cellular responses have been identified to different regions of the HBV nucleocapsid core and surface antigens. T cell mediated immunity, particularly involving class I major histocompatibility complex (MHC)-restricted cytotoxic T lymphocytes (CTL), is believed to play an important role in resistance to hepatitis as well as several other viral infections. CTL recognize antigen in the form of small peptides in association with the class I histocompatibility molecules. The antigen-specific CTL, when stimulated, can secrete mediators which inhibit viral replication and eliminate infected cells, thereby contributing to an individual's recovery from the infection. Although studies suggest that the T cell repertoire of class I-restricted responses is focused on a limited number of discrete immunodominant epitopes of a viral protein (Braciale et al., *Proc. Natl. Acad. Sci. USA* 86:277–281 (1989)), for many viruses, including the hepatitis viruses and particularly HBV, few epitopes have been identified. See also Barnaba et al., *Nature* 345:258 (1990) have identified an A11 restricted epitope while Jin et al., *J. Exp. Med.* 168:293 (1988) have identified an A3 restricted epitope. Aichele et al., *J. Exp. Med.* 171:1815–1820 (1990), have demonstrated induction in vivo of an antiviral CTL response in an MHC class-I dependent fashion with a peptide from the nucleoprotein of lymphocytic choriomeningitis virus. Recently, Kast et al., *Proc. Natl. Acad. Sci. USA* 88:2283–2287 (1991), described in stimulation of Sendai virus-specific CTL in vivo using free synthetic peptide derived from the nucleoprotein to confer protection against subsequent viral challenge.

It has been suggested that hepatocyte injury during HBV infection may be mediated by an HLA class I-restricted CTL response to HBV antigen. In attempting to define the CTL response to HBV, it has been shown that peripheral blood lymphocytes from patients with acute and chronic HBV may be able to kill autologous hepatocytes in vitro, but the specificity of the cytolytic activity, its HLA restriction elements, and cellular phenotype were not established. See, Mondelli et al., *J. Immunol.* 129:2773 (1982) and Mondelli et al., *Clin. Exp. Immunol.* 6:311 (1987). More recently, Moriyama et al., *Science* 248:361–364 (1990), reported that the HBV major envelope antigen was expressed at the hepatocyte surface in a form recognizable by MHC class I-restricted, $CD8^+$ cytotoxic T lymphocytes, and by envelope-specific antibodies. However, the HBV epitopic regions responsible for HBV-specific CTL activity were not identified.

The requirement for lympholines such as IL-2 in the generation of CD8+ CTL is well established, although the need for activation of CD4+ T helper cells to provide these lymphokines remains somewhat controversial. While the concept of linked T helper-B cell recognition for antibody production has been firmly defined, there is no compelling evidence for linked T helper-CTL recognition for the in vivo induction of CD8+ CTL. See, e.g., Buller et al., *Nature* 328:77–79 (1987); Sarobe et al., *Eur. J. Immunol.* 21:1555–1558 (1991); and Cassell and Forman, *Annals N.Y. Acad. Sci.* :51–60 (1991).

Individuals chronically infected with HBV are at risk of developing liver cirrhosis and/or hepatocellular carcinoma, and constitute an extremely large reservoir for spreading the disease. It would be desirable to stimulate the immune systems of those chronically infected to respond to appropriate HBV antigens and eliminate their infections, or to be able to prevent the evolution from an acute HBV infection to the chronic stage. Further, as the presently approved HBV vaccines provide only about 90% protection among these immunized, it is desirable to improve the existing vaccines by increasing or diversifying the immunogenicity of the vaccines to elicit a more effective immunity. Means are also needed for predicting which patients with acute HBV infection are likely to develop chronic HBV infection, so that appropriate treatment and precautions can be implemented earlier. Quite surprisingly, the present invention fulfills these and other related needs.

SUMMARY OF THE INVENTION

The present invention provides peptides which induce MHC class I-restricted CTL responses against HBV antigen. The peptides of interest are derived from sequences of the HBV surface antigen or nucleocapsid proteins. In certain embodiments the peptides comprise from six to about thirty amino acids and contain at least one epitope which is capable of inducing a MHC class I-restricted cytotoxic CTL response to HBV where the epitope(s) is within the HBV envelope antigen sequence designated 799.10 ($HBenv_{349-368}$) [Seq. ID NO. 2] Leu-Ser-Pro-Thr-Val-Trp-Leu-Ser-Val-Ile-Trp-Met-Met-Trp-Tyr-Trp-Gly-Pro-Ser-Leu or 799.09 ($HBenv_{329-348}$) [Seq. ID No. 7] Ala-Ser-Ala-Arg-Phe-Ser-Trp-Leu-Ser-Leu-Leu-Val-Pro-Phe-Val-Gln-Trp-Phe-Val- Gly (for subtypes ayw and adw). Other peptide embodiments comprise from six to thirty amino acids and have at least seven amino acids from the HBenv sequence 799.08 (HBenv$_{309-328}$) [Seq. ID No. 1] Asn-Cys-Thr-Cys-Ile-Pro-Ile-Pro-Ser-Ser-Trp-Ala-Phe-Gly-Lys-Phe-Leu-Trp-Glu-Trp (for subtype ayw). In yet other embodiments a peptide is derived from HBV core antigen sequence region designated 802.03 (HBc$_{91-110}$) [Seq. ID No. 4], having the sequence Thr-Asn-Met-Gly-Leu-Lys-Phe-Arg-Gln-Leu-Leu-Trp-Phe-His-Ile-Ser-Cys-Leu-Thr-Phe (subtype ayw). The peptides of the invention can be optionally flanked and/or modified at one or both of the N- and C-termini, as desired, and substitutions, deletions and additions may be made to the peptide as long as the ability of the peptide to stimulate HBV CTL activity or act as an analog antagonist is not substantially adversely affected.

In the various peptide embodiments it will be understood that the peptides can be covalently linked, e.g., via polymerization or conjugation, each to itself to form larger homopolymers, or with different peptides to form heteropolymers. In some instances peptides will be combined in a composition as an admixture and will not be linked. The CTL inducing peptide can also be linked to a lipid-containing molecule capable of enhancing a T lymphocyte response, or may be linked to a T helper peptide which induces a T-helper cell response, or may be linked to both a lipid-containing molecule and a T helper peptide, for example. Linkage to a lipid or a T-helper peptide may be either at the amino or carboxy termini.

Compositions are provided which comprise a peptide of the invention formulated with an additional peptide, a liposome, an adjuvant and/or a pharmaceutically acceptable carrier. Thus, pharmaceutical compositions can be used in methods of treating acute HBV infection, particularly in an effort to prevent the infection from progressing to a chronic or carrier state. Methods for treating chronic HBV infection and HBV carrier states are also provided, where the pharmaceutical compositions are administered to infected individuals in amounts sufficient to stimulate immunogenically effective CTL responses against HBs and HBc epitopes. For treating these infections it may be particularly desirable to combine the peptides which induce MHC class I restricted CTL responses against HBV antigen with other peptides or proteins that induce immune response to other HBV antigens. To treat individuals with chronic or carrier state infections the compositions may be administered with an initial dosage followed by a boosting dosage over a period of time, as necessary to resolve or substantially mitigate the infection.

Vaccine compositions for preventing HBV infection, including preventing development of chronic HBV infection from an acute infection, are also provided. The vaccine compositions comprise an immunogenically effective amount of a HBV peptide which induces a MHC class I restricted CTL response. In the case of HLA-A2 haplotype individuals, the peptide can be derived from any of peptides 799.08 (HBenv$_{309-328}$) [Seq. ID No. 1], 799.09 (HBenv$_{329-348}$) [Seq. ID No. 7], 799.10 (HBenv$_{349-368}$) [Seq. ID NO. 2], and/or 802.03 (HBc$_{91-110}$) [Seq. ID No. 4], and will typically further comprise an adjuvant, e.g, incomplete Freund's adjuvant, aluminum hydroxide, or the like. To achieve enhanced protection against HBV, the vaccine can further comprise additional components to elicit protective cellular and/or antibody responses to HBV antigens. In preferred embodiments the CTL inducing peptides are administered with one or more T helper peptides which contain T helper epitopes. Selection of the T helper peptide depends upon whether the vaccine composition containing a T helper peptide is administered prophylactically or therapeutically. In the case of prophylactic administration the T helper peptide will be one or more HBV peptides derived from the HBV envelope or core or proteins derived from other organisms such as tetanus toxoid, influenza, parainfluenza, malaria, Epstein Barr virus, herpes simplex and others known to one of ordinary skill in the art. In the case of therapeutic administration the T helper epitope will preferably be peptides selected from proteins derived from infectious agents other than HBV. Several examples of T helper peptide are HBc128-140, HBc1-20, HBc50-69 and HBc111-125 tetanus toxoid 830-843 and influenza 307-319. The T helper peptides may be administered simulataneously or separately with the CTL-including peptide, but preferably the CTL and T helper peptides are linked. The linkage of the peptides may comprise a spacer molecule, such as amino acids residues, e.g., alanine or other relatively neutral residues.

In yet other embodiments the invention relates to methods for diagnosis, where the peptides of the invention are used to determine the presence in an individual of lymphocytes which are capable of a cytotoxic T cell response to HBV surface or nucleocapsid antigen. The absence of such cells determines whether the individual of interest is susceptible to developing chronic HBV infection. Typically the lymphocytes are peripheral blood lymphocytes and the individual of interest is suffering from an acute HBV infection.

DESCRIPTION OF THE SPECIFIC EMBODIMENTS

Figure 1A:
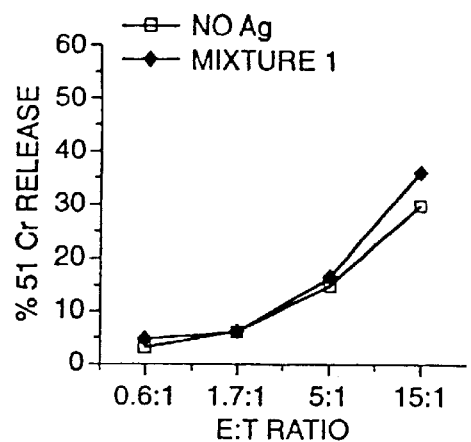
FIG. 1 depicts the results of induction of HBV peptide-specific A2.1-restricted CTL by priming A2.1/K$^b$ transgenic mice with syngeneic spleen cells "loaded" with HBV. Panels A–D: Splenocytes from HBV-primed transgenic mice were restimulated in vitro with four mixtures of syngeneic LPS blasts each coated with one of 13 different peptides. After 9 days effector cells were assayed for lytic activity against $^{51}$Cr labelled Jurkat A2.1/K$^b$ target cells in the presence or absence of the four different peptide mixtures used for induction. Panels E–H: Effector cells raised against the four different peptide mixtures were restimulated in vitro against the same peptide mixtures and assayed for lytic activity against $^{51}$Cr labelled Jurkat A2.1/K$^b$ target cells in the presence or absence of the individual peptides.
Figure 1B:
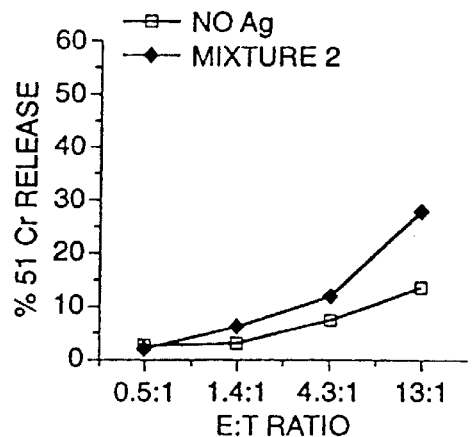
Figure 1C:
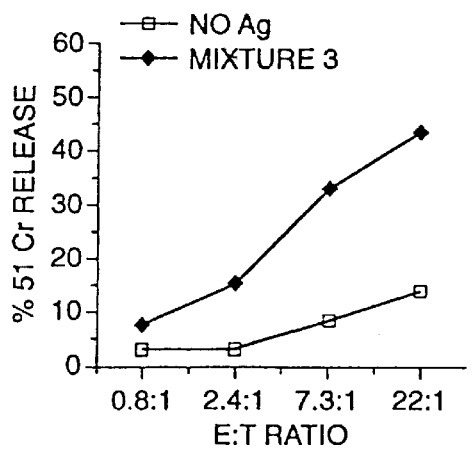
Figure 1D:
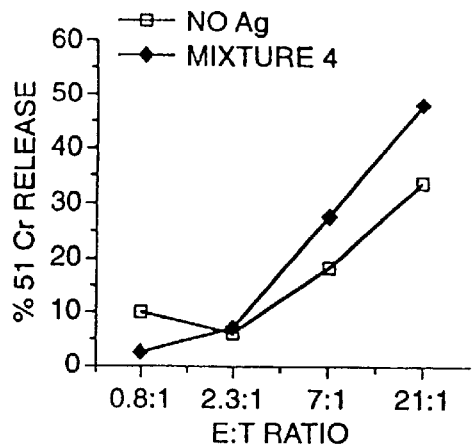
Figure 1E:
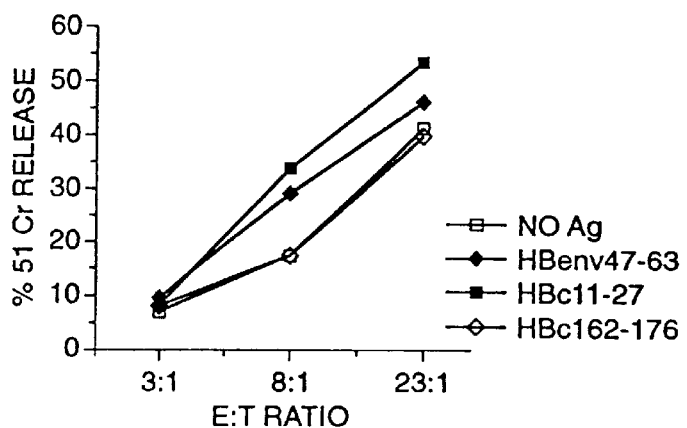
Figure 1F:
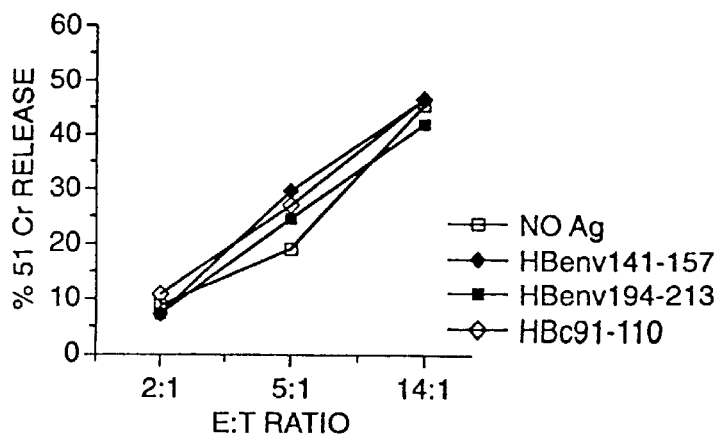
Figure 1G:
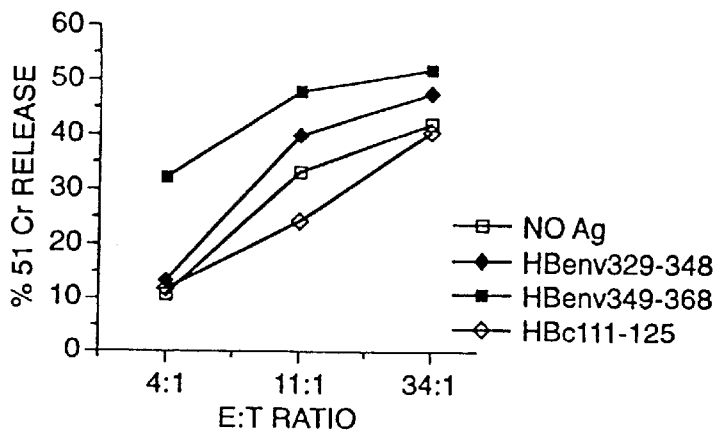
Figure 1H:
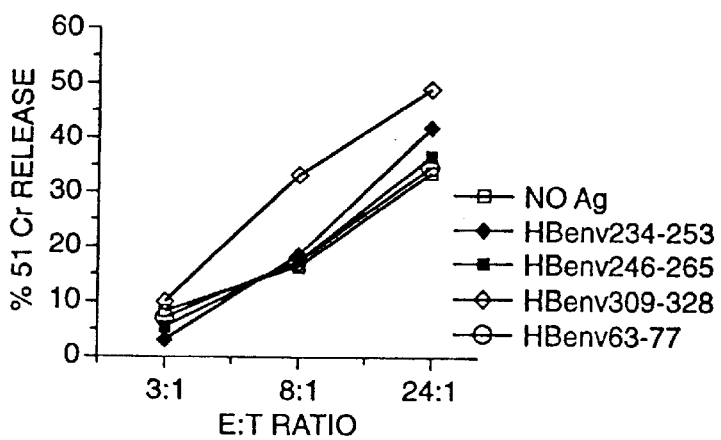
Figure 2I:
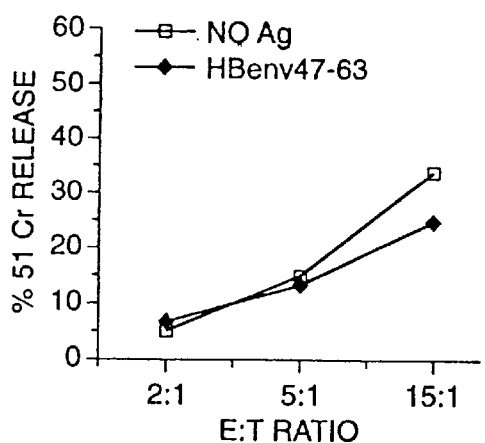
FIGS. 2I to P collectively illustrates the HBV peptide specificity of A2.1 transgenic CTL. Transgenic CTL raised from HBV-primed transgenic mice and restimulated in vitro twice with one of the four different peptide mixtures were restimulated with individual HBV peptides and assayed for lytic activity on $^{51}$CR labelled Jurkat target cells in the presence or absence of the HBV peptides used for the restimulation.
Figure 2J:
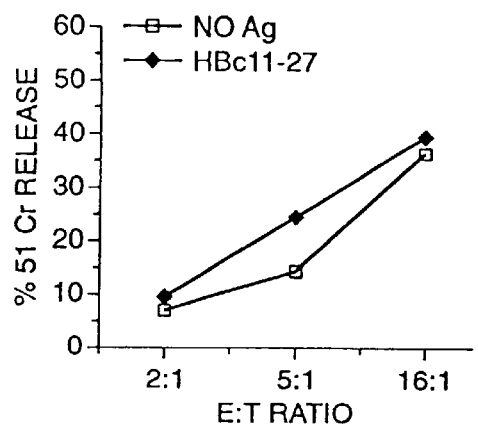
Figure 2K:
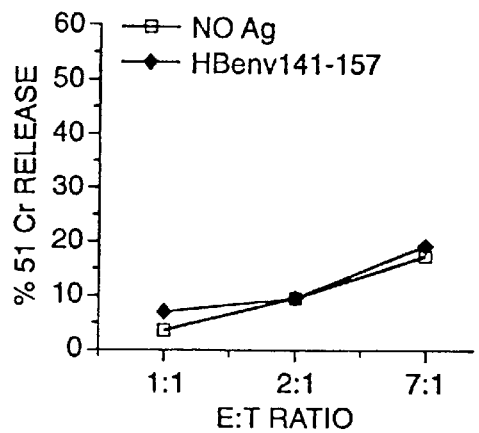
Figure 2L:
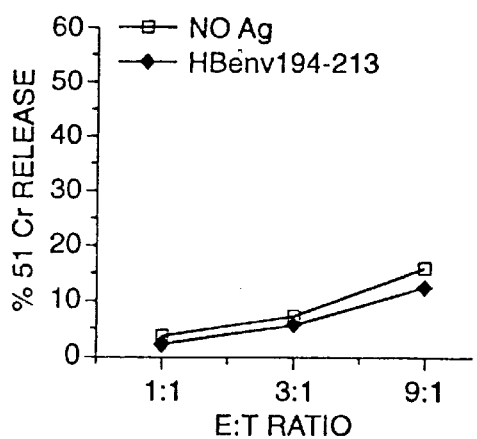
Figure 2M:
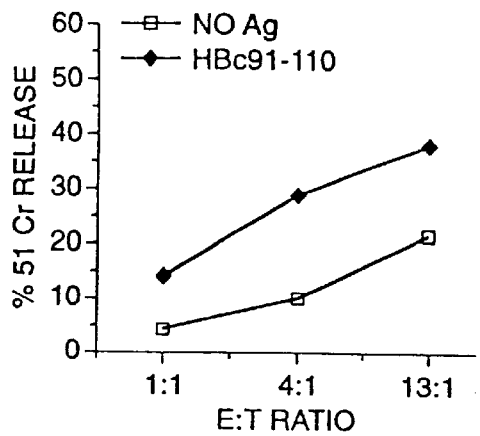
Figure 2N:
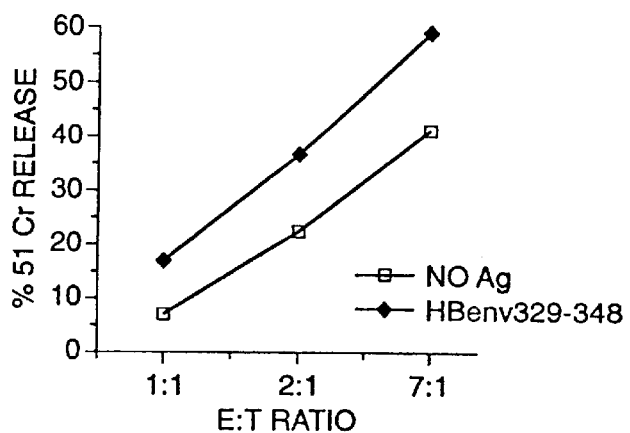
Figure 2O:
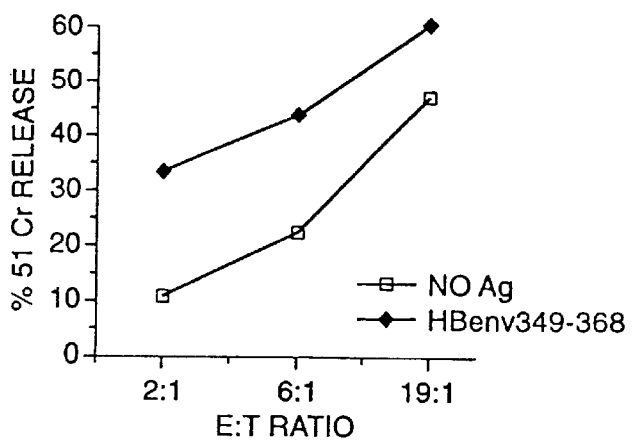
Figure 2P:
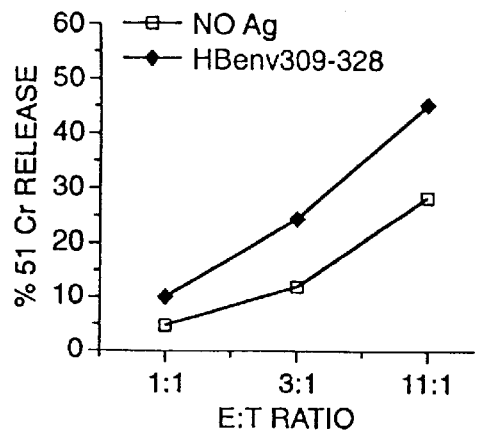
Figure 3A:
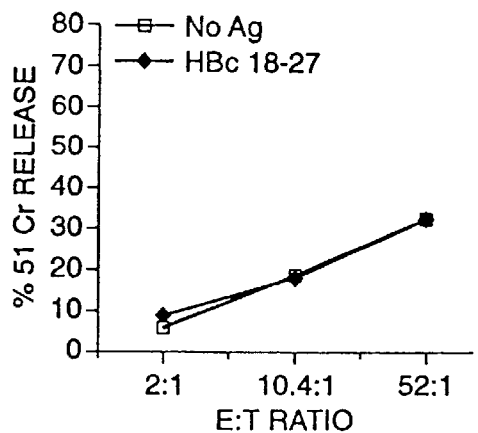
FIGS. 3A to L collectively illustrates the results of induction of HBV peptide-specific A2.1-restricted CTL by priming A2.1/K$^b$ transgenic mice with HBV in IFA. A. Splenocytes from HBV-primed transgenic mice were restimulated in vitro with syngeneic LPS blasts coated with HBV peptides. After 6d, effector cells were assayed for lytic activity against $^{51}$Cr labelled Jurkat A2.1/K$^b$ target cells in the presence or absence of the appropriate HBV peptide. Each panel represents the CTL activity induced by the indicated target peptide.
Figure 3B:
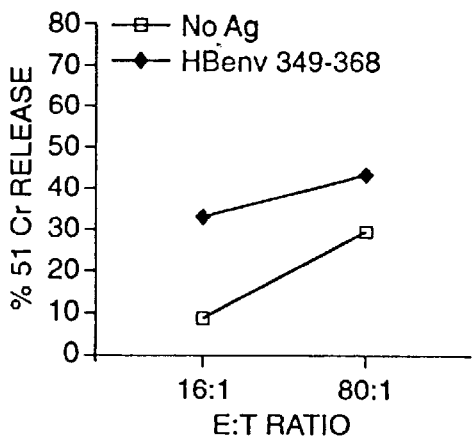
Figure 3C:
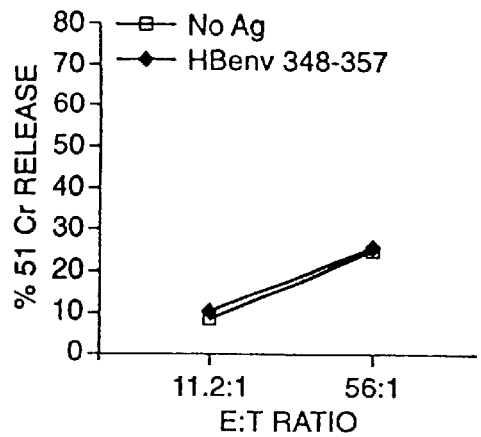
Figure 3D:
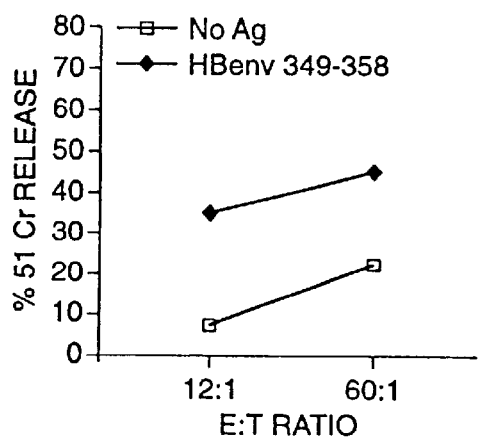
Figure 3E:
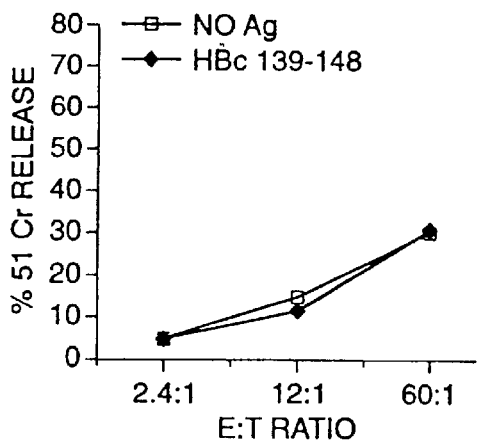
Figure 3F:
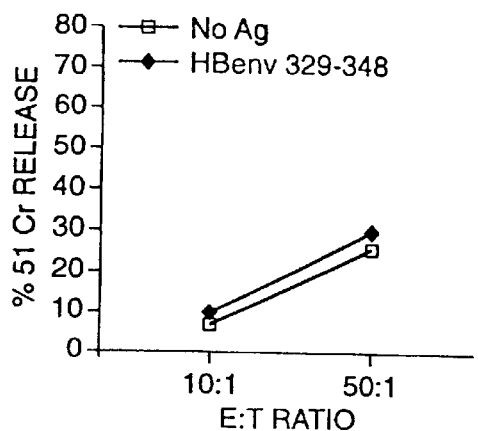
Figure 3G:
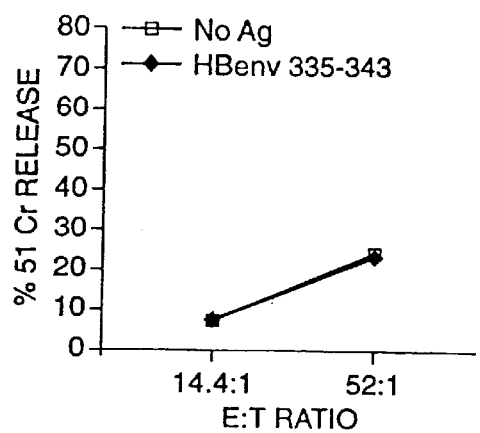
Figure 3H:
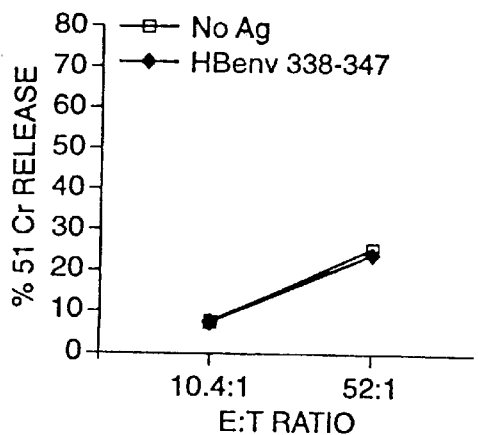
Figure 3I:
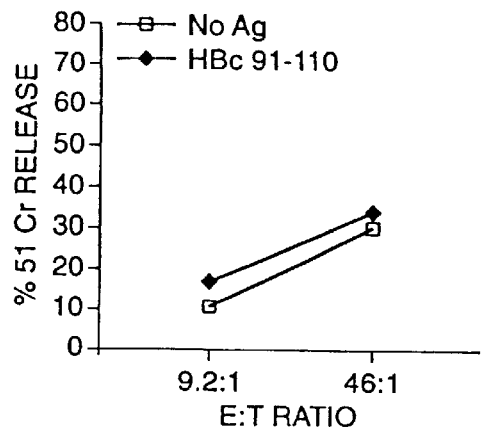
Figure 3J:
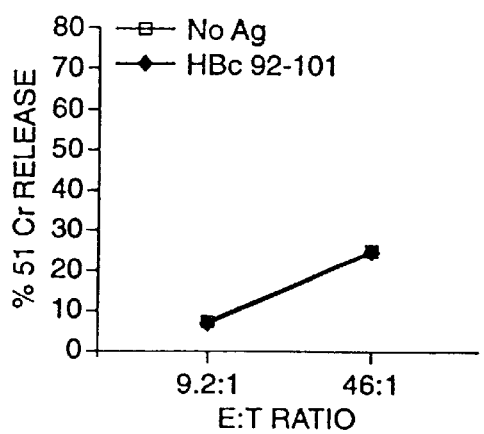
Figure 3K:
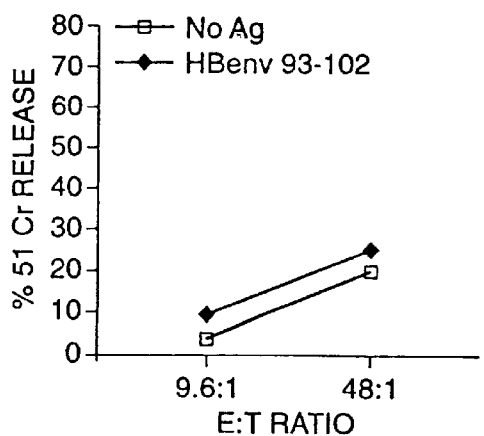
Figure 3L:
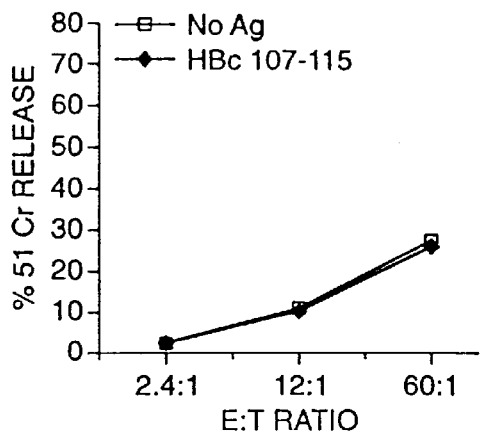
Figure 4A:
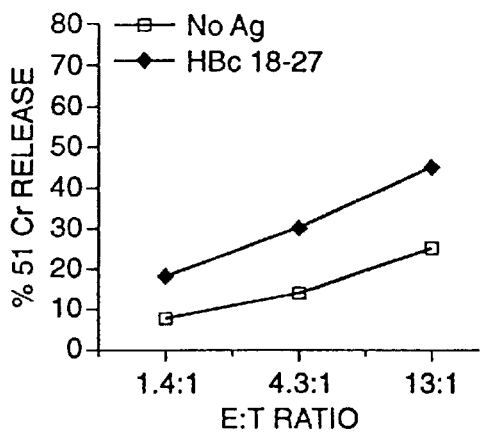
FIGS. 4 A–L collectively show results obtained when the effector CTL of FIG. 3 were restimulated with peptide coated LPS blasts followed at a one week interval by restimulation with peptide coated Jurkat A2.1/K$^b$ cells. Six days after the last restimulation, effector cells were assayed for cytolytic activity against $^{51}$Cr labelled Jurkat A2.1/K$^b$ target cells in the absence or presence of the peptide used for the restimulation, plus related peptides. Each panel represents the CTL activity induced by the peptide indicated in the corresponding panel of FIG. 3. The target peptides are indicated in each panel.
Figure 4B:
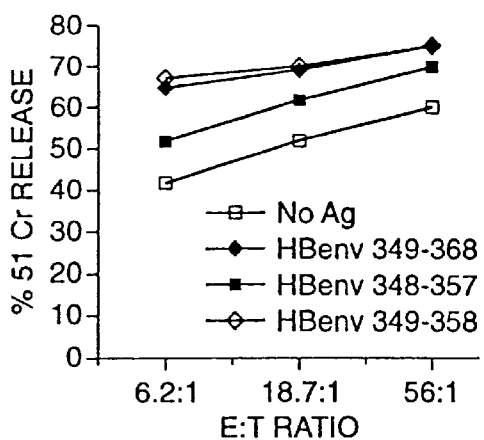
Figure 4C:
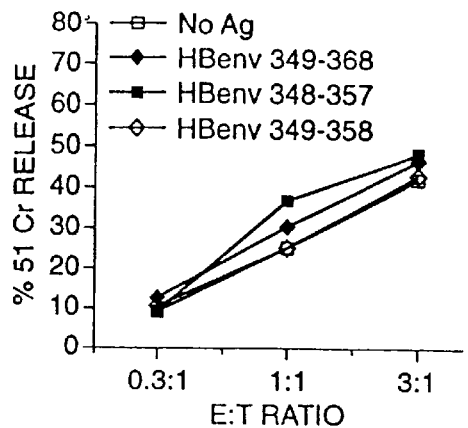
Figure 4D:
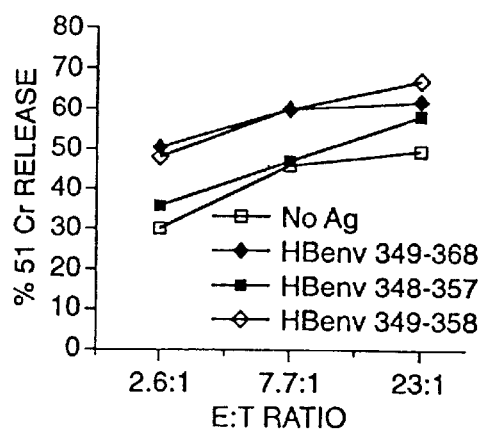
Figure 4E:
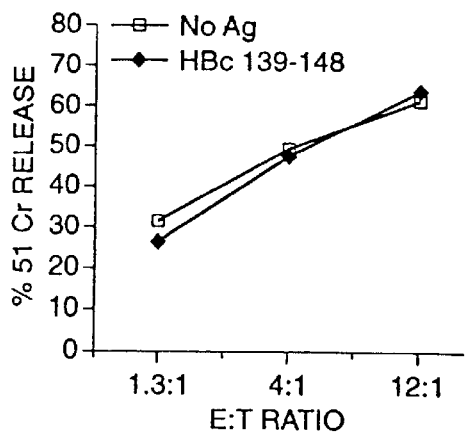
Figure 4F:
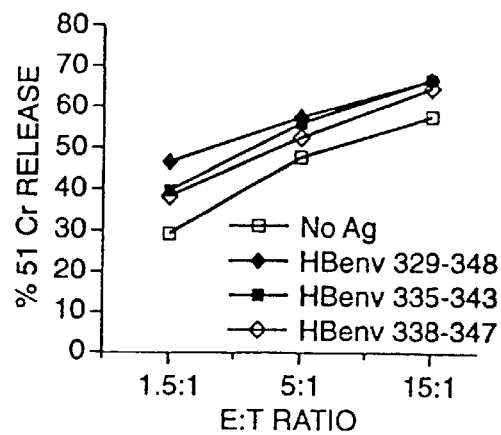
Figure 4G:
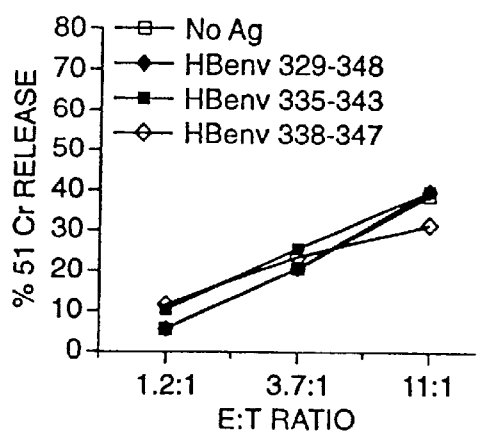
Figure 4H:
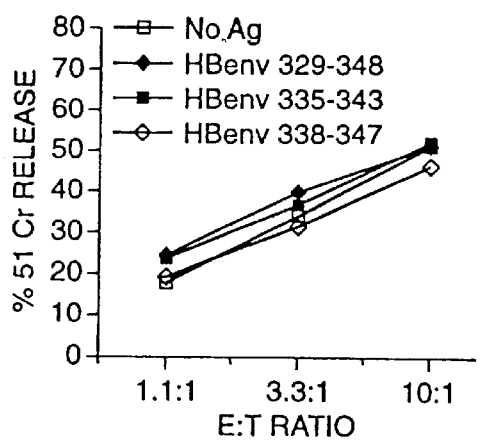
Figure 4I:
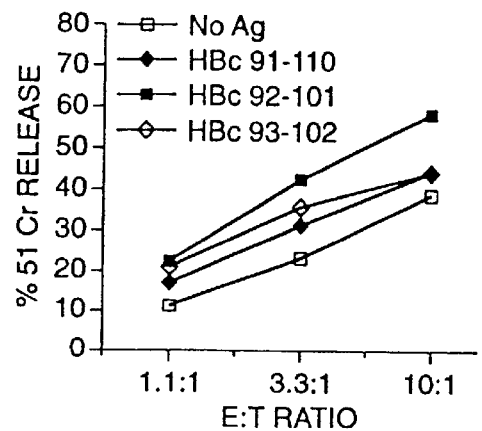
Figure 4J:
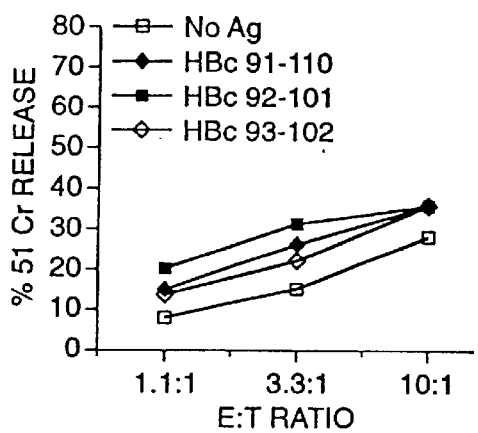
Figure 4K:
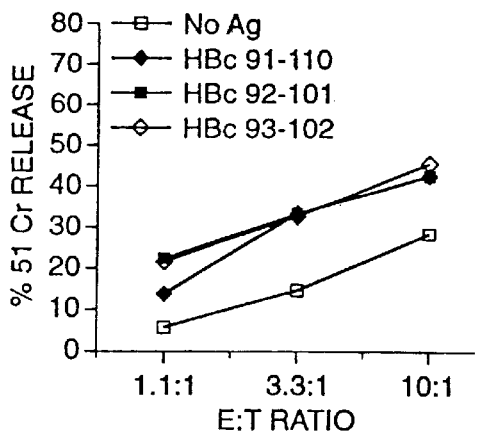
Figure 4I:
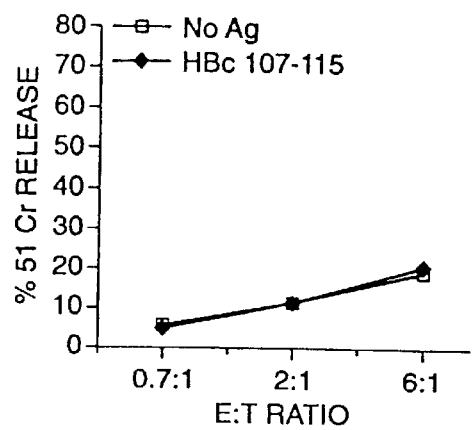

The present invention provides peptides derived from the HBV envelope antigen (HBenv, also referred to as surface antigen, or HBs) and nucleocapsid core (HBc) protein sequences for use in compositions and methods for the treatment, prevention and diagnosis of HBV infection. The peptides are capable of inducing MHC HLA class I-restricted CTL responses to HBV infected cells. The stimulated CTL, which secrete lymphokines (e.g., gamma interferon) and liberate products (e.g., proteolytic enzymes such as serine esterases) that inhibit viral replication in infected autologous cells or transfected cells, with or without cell killing, are able to interrupt or substantially prevent chronic HBV infection. In many instances the combination of an effective cytotoxic T cell response and a protective antibody response to selected HBV antigens will be most effective in preventing or terminating an HBV infection.

In preferred embodiments the peptides of the invention are derived from within the HBV surface antigen or the nucleocapsid polypeptides, core and precore. In more preferred embodiments described herein CTL-inducing peptides are derived from the region of HBenv$_{309-328}$ (peptide 799.08), HBenv$_{329-348}$ (peptide 799.09) HBenv$_{349-368}$ (peptide 799.01), or the region HBc$_{91-110}$ (peptide 802.03), where the numbering is according to Galibert et al., Nature 281:646 (1979), which is incorporated herein by reference.

By "CTL inducing peptide" or "oligopeptide" of the present invention is meant a chain of at least four amino acid residues, preferably at least six, more preferably eight to ten, sometimes eleven to fourteen residues, and usually fewer than about thirty residues, more usually fewer than about twenty-five, and preferably fewer than fifteen, e.g., eight to fourteen amino acid residues derived from selected epitopic regions of the HBenv of HBc proteins, or such other epitopic regions of other potential target antigens, such as tumor associated antigens, including, but not limited to, renal cell carcinoma, breast cancer, carcinoembryonic antigens, melanoma (MAGE-1) antigens, and prostate cancer specific antigen, hepatitis C antigens, Epstein-Barr virus antigens, HIV-1 and HIV-2 antigens, and papilloma virus antigens.

With respect to hepatitis B, as set forth in more detail below, usually at least four, sometimes six, often seven or more residues of the peptide or a majority of amino acids of that peptide will be identical or homologous when compared to the corresponding portion of the naturally occurring HBenv sequence identified as HBenv$_{309-328}$ (peptide 799.08) or HBenv$_{329-349}$ (peptide 799.09) or HBenv$_{349-368}$ (peptide 799.10), or the HBc region HBc$_{91-110}$ (peptide 802.03).

The peptides can be prepared "synthetically," as described hereinbelow, or by recombinant DNA technology. Although the peptide will preferably be substantially free of other naturally occurring HBV proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

homology is calculated by comparing one to another when aligned to corresponding portions of the reference sequence.

A CTL inducing HBenv peptide embodiment of the invention comprises from six to thirty amino acids and is derived from the 799.08 peptide region $HBenv_{309-328}$, contains a CTL epitopic site(s), and has at least seven amino acids wherein a majority of amino acids of the peptide will be identical or substantially homologous, when compared to the amino acids comprising the corresponding portion of the naturally occurring $HBenv_{309-328}$ sequence. A representative peptide of this region is peptide $HBenv_{309-328}$, which has the following sequence (for HBV subtype ayw):

799.08 ($HBenv_{309-328}$) [Seq. ID No. 1]

Asn-Cys-Thr Cys-Ile-Pro-Ile-Pro-Ser-Ser-Trp-Ala-

Phe-Gly-Lys-Phe-Leu-Trp-GlU-Trp

Desirably, the peptide will be as small as possible while still maintaining substantially all of the biological activity of the large peptide. When possible, it may be desirable to optimize peptides of the invention to a length of eight to twelve amino acid residues, commensurate in size with endogenously processed viral peptides that are bound to MHC class I molecules on the cell surface. See generally, Schumacher et al., *Nature* 350:703–706 (1991); Van Bleek et al., *Nature* 348:213–216 (1990); Rotzschke et al., *Nature* 348:252–254 (1990); and Falk et al., *Nature* 351:290–296 (1991), which are incorporated herein by reference. By biological activity is meant the ability to bind an appropriate MHC molecule and, in the case of peptides useful for stimulating CTL responses, induce a CTL response against HBV antigen or antigen mimetic. In the case of a peptide analog antagonist, the analog will have biological activity if it competes with the peptide for binding to the MHC molecule and has a substantially reduced ability to stimulate a CTL response when compared to the native peptide. By a CTL response is meant a $CD8^+$ T lymphocyte response specific for an HBV antigen of interest, wherein $CD8^+$, MHC class I-restricted T lymphocytes are activated. As noted above, the activated T lymphocytes will secrete a variety of products which inhibit viral replication and may or may not kill the HBV infected (or transfected) cell.

The terms "homologous", "substantially homologous", and "substantial homology" as used herein denote a sequence of amino acids having at least 50% identity wherein one sequence is compared to a reference sequence of amino acids. The percentage of sequence identity or wherein the peptide can be optionally flanked and/or modified at one or both of the N- and C-termini, as desired, by amino acids from HBV sequences, particularly HBenv, amino acids added to facilitate linking, other N- and C-terminal modifications, linked to carriers, etc., as further described herein. For a peptide of the HBV subtype adw, $Gly_{322}$ is replaced by Ala, and $Phe_{324}$ is replaced by Tyr. The peptide $HBenv_{309-328}$ induces a CTL response which is mediated by at least the MHC class I molecule HLA-A2.

Another HBenv CTL inducing peptide embodiment of the invention comprises from six to twenty amino acids of the 799.10 peptide region $HBenv_{349-368}$, and includes peptides derived from $HBenv_{349-368}$ which contain an epitopic site(s) of at least seven or more amino acids where a majority of amino acids of the peptide will be identical or homologous when compared to the corresponding portion of the naturally occurring HBenv sequence identified as $HBenv_{349-368}$, which is as follows (for HBV subtypes ayw and adw):

799.10 ($HBenv_{349-368}$) [Seq. ID No. 2]

Leu-Ser-Pro-Thr-Val-Trp-Leu-Ser-Val-Ile-

Trp-Met-Met-Trp-Tyr-Trp-Gly-Pro-Ser-Leu wherein the peptide selected from said region can be flanked and/or modified at one or both termini as described herein. An example of another CTL inducing peptide derived from the region of 799.10 ($HBenv_{349-368}$) [Seq. ID No. 2] which contains at least one epitope capable of inducing a MHC release I-restricted cytotoxic T-lymphocyte response to hepatitis B virus is:

884.02 ($HBenv_{349-358}$) [Seq. ID No. 3]

Leu-Ser-Pro-Thr-Val-Trp-Leu-Ser-Val-Ile.

Yet other CTL-inducing peptide embodiments of the invention are derived from the HBenv region $HBenv_{329-348}$. In addition to peptide 799.09 ($HBenv_{329-348}$), these embodiments include peptides which contain an epitopic site(s) within the sequence of $HBenv_{329-348}$ which is capable of inducing a MHC class I-restricted CRL response to HBV. $HBenv_{329-348}$ for HBV subtype ayw has the following sequence:

799.09 (HBenv$_{329-348}$)  [Seq. ID No. 7]

Ala-Ser-Ala-Arg-Phe-Ser-Trp-Leu-Ser-Leu-Leu-Val-Pro-Phe-Val-

Gln-Trp-Phe-Val-Gly.

In further embodiments, peptides of the invention are drived from the HBc region HBc$_{91-110}$, and besides peptide 802.03 (HBc$_{91-110}$) includes peptides which contain an epitopic site(s) of at least seven and preferably nine amino acids wherein a majority of amino acids of the peptide will be identical or substantially homologous when compared to the amino acids of corresponding portion of the naturally occurring HBc sequence of HBc$_{91-110}$, wherein the sequence for HBc$_{91-110}$ for HBV subtype ayw has the following sequence:

e.g., improved pharmacological characteristics, while increasing or at least retaining substantially all of the biological activity of the unmodified peptide. For instance, the peptides can be modified by extending, decreasing or substituting in the peptides amino acid sequences by, e.g., the addition or deletion of amino acids on either the amino terminal or carboxy terminal end, or both, of peptides derived from the sequences disclosed herein. As further described below, the CTL activity of the subject peptides can be enhanced by linkage to a sequence which contains at least 802.03 (HBc$_{91-110}$)  [Seq. ID NO. 4]

Thr-ASn-Met-Gly-Leu-Lys-Phe-Arg-Gln-Leu-

Leu-Trp-Phe-His-Ile-Ser-Cys-Leu-Thr-Phe wherein the peptide selected from said region can be flanked and/or modified at one or both termini as described herein. For a peptide of the HBV subtype adw, Phe$_{97}$ is replaced by Ile, and Leu$_{101}$ is replaced by Trp. The CTL inducing peptide 802.03 induces a CTL response which is mediated by at least the MHC class I molecule HLA-A2.1. Examples of CTL inducing peptides derived from the region of 802.03 (HBc$_{91-110}$) [Seq. ID No. 4] and which contain an epitope capable of inducing a MHC class I-restricted cytotoxic T-lymphocyte response to hepatitis B virus include the following:

one epitope that is capable of inducing a T helper cell response, such as contained within a T helper peptide provided by peptides from tetanus toxoid 830-843, influenza 307-319, malaria circumsporozoite 382-398 and 378-389, ovalbumin 323-336, and HBc128-140, HBc1-20, HBc50-69 and HBc111-125.

The peptides employed in the subject invention need not be identical to peptides 799.08, 799.09, 799.110 or 802.03, or to a particular HBV surface antigen or nucleocapsid protein sequence, so long as the subject compounds are able to bind to the appropriate MHC molecule and provide for 883.02 (HBc$_{92-101}$)  [Seq. ID No. 5]

Asn-Met-Gly-Leu-Lys-Phe-Arg-Gln-Leu-Leu, (HBc$_{92-100}$)  [Seq. ID No. 9]

Asn-Met-Gly-Leu-Lys-Phe-Arg-Gln-Leu, and 883.03 (HBc$_{93-102}$)  [Seq. ID No. 6]

Met-Gly-Leu-Lys-Phe-Arg-Gln-Leu-Leu-Trp.

As mentioned above, additional amino acids can be added to the termini of an oligopeptide or peptide to provide for ease of linking peptides one to another, for coupling to a carrier, support or larger peptide, for reasons discussed herein, for modifying the physical or chemical properties of the peptide or oligopeptide, or the like. Amino acids such as tyrosine, cysteine, lysine, glutamic or aspartic acid, or the like, can be introduced at the C- the N-terminus of the peptide or oligopeptide. In addition, the peptide or oligopeptide sequences can differ from the natural sequence by being modified by terminal-NH$_2$ acylation, e.g., by alkanoyl ($C_1$–$C_{20}$) or thioglycolyl acetylation, terminal-carboxy amidation, e.g., ammonia, methylamine, etc. In some instances these modifications may provide sites for linking to a support or other molecule.

It will be understood that the peptides of the present invention or analogs thereof which have CTL stimulating activity may be modified to provide other desired attributes, cytotoxic T lymphocytic activity against at least one of the four major subtypes of HBV (except in the case of peptide analog antagonists, which bind the MHC molecule but have a substantially reduced ability to stimulate CTL activity, as explained further herein). Therefore, the peptides may be subject to various changes, such as insertions, deletions, and substitutions, either conservative or non-conservative, where such changes might provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an HBV CTL stimulating epitope will not differ by more than about 20% from the sequence of at least one subtype of HBV, except where additional amino acids may be added at either terminus for the purpose of modifying the physical or chemical properties of the peptide for, e.g., ease of linking or coupling, and the like. In those situations where regions of the peptide sequences are found to be polymorphic among HBV subtypes, it may be desirable to vary one or more particular amino acids to more effectively mimic differing cytotoxic T-lymphocyte epitopes of different HBV strains or subtypes.

Within the peptide sequence regions identified by the present invention as containing CTL epitopes, e.g., peptide region 799.08 (HBenv$_{309-328}$), peptide region 799.09 (HBenv$_{329-348}$) peptide region 799.10 (HBenv$_{349-368}$), or peptide region 802.03 (HBc$_{91-110}$), there are residues (or those which are substantially functionally equivalent) which allow the peptide to retain their biological activity, i.e., the ability to stimulate a class I-restricted cytotoxic T-lymphocytic response against HBV infected cells or cells which express HBV surface and/or nucleocapsid antigens. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a CTL can also be achieved by such alterations. Generally, any spacer substitutions, additions or deletions between epitopic and/or conformationally important residues should employ amino acids or other moieties chosen to avoid steric and charge interference which might disrupt binding.

Peptides which tolerate substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptides. Further, L-amino acid-containing peptides with or without substitutions can be capped with a D-amino acid to inhibit exopeptidase destruction of the antigenic peptide.

Having identified different peptides of the invention which contribute to stimulating HBV specific CTL responses in one or more patients or HLA types, in some instances it may be desirable to join two or more peptides in a composition. The peptides in the composition can be identical or different, and together they should provide equivalent or greater biological activity than the parent peptide(s). For example, using the methods described herein, two or more peptides may define different or overlapping CTL epitopes from a particular region, e.g., the peptide region 799.08 (HBenv$_{309-328}$), peptide region, 799.09 (HBenv$_{329-349}$), 799.10 (HBenv$_{349-368}$), or peptide region 802.03 (HBc$_{91-110}$), which peptides can be combined in a "cocktail" to provide enhanced immunogenicity for CTL responses. Peptides of one region can also be combined with peptides having different MHC restriction elements. This composition can be used to effectively broaden the immunological coverage provided by therapeutic, vaccine or diagnostic methods and compositions of the invention among a diverse population.

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different HBV subtypes, different epitopes within a subtype, different HLA restriction specificities, or peptides which contain T helper epitopes, heteropolymers with repeating units are provided. In addition to covalent linkages, noncovalent linkages capable of forming intermolecular and intrastructural bonds are also contemplated.

Linkages for homo- or hetero-polymers or for coupling to carriers can be provided in a variety of ways. For example, cysteine residues can be added at both the amino- and carboxy-termini, where the peptides are covalently bonded via controlled oxidation of the cystein residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, Immun. Rev. 62:185 (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl) cyclohexane-1-carboxylate (SMCC). Of course, it will be understood that linkage should not substantially interfere with either of the linked groups to function as described, e.g., to function as an HBV cyctotoxic T cell determinant, peptide analog CTL antagonist, or HBV T helper determinant.

In another aspect the peptides of the invention can be combined or coupled with other peptides which present HBV T-helper cell epitopes, i.e., T helper peptides comprising six to thirty amino acids containing a T helper epitope which from the envelope, core or other immunogenic protein or derivative thereof, stimulate T cells that cooperate in the induction of cytotoxic T cells to HBV. The T-helper cells can be either the T-helper 1 or T-helper 2 phenotype, for example. Compositions of T-helper peptides and CTL peptides thereby enhance an individual's immunity by providing cell-mediated immunity and protective antibodies to HBV. T-helper epitopes have been identified as HBc$_{1-20}$, having the sequence: Met-Asp-Ile-Asp-Pro-Tyr-Lys-Glu-Phe-Gly-Ala-Thr-Val-Glu-Leu-Leu-Ser-Phe-Leu-Pro [Seq. ID No. 10]. Other T-helper epitopes are provided by peptides from the region HBc$_{50-69}$, having the sequence Pro-His-His-Tyr-Ala-Leu-Arg-Gln-Ala-Ile-Leu-Cys-Trp-Gly-Glu-Leu-Met-Tyr-Leu-Ala [Seq. ID No. 11], and from the region of HBc$_{100-139}$, including HBc$_{100-119}$ having the sequence Leu-Leu-Trp-Phe-His-Ile-Ser-Cys-Leu-Thr-Phe-Gly-Arg-Glu-Thr-Val-Ile-Glu-Tyr-Leu [Seq. ID No. 12] (where Ile$_{116}$ is Leu in the HBV adw subtype), HBc$_{117-131}$ having the sequence Gly-Tyr-Leu-Val-Ser-Phe-Gly-Val-Trp-Ile-Arg-Thr-Pro-Pro-Ala [Seq. ID No. 13], and peptide HBc$_{120-139}$ having the sequence Val-Ser-Phe-Gly-Val-Trp-Ile-Arg-Thr-Pro-Pro-Ala-Tyr-Arg-Pro-Pro-Asn-Ala-Pro-Ile [Seq. ID No. 14]. See, Ferrari et al., *J. Clin. Invest.* 88:214–222 (1991), and U.S. Pat. No. 4,882,145, each of which is incorporated herein by reference. Other T helper epitopes are provided by peptides from, for example, tetanus toxoid $_{830-843}$ having the sequence Gln-Tyr-Ile-Lys-Ala-Asn-Ser-Lys-Phe-Ile-Gly-Ile-Thr-Glu (QYIKANSKFIGITE) [Seq. ID No. 15]; malaria circumsporozoite $_{382-398}$ Lys-Ile-Ala-Lys-Met-Lys-Ala-Ser-Ser-Val-Phe-Asn-Val-Val-Asn-Ser (KIAKMEKASSVFNVVNS) [Seq. ID No. 16]; malaria circumsporozoite $_{378-398}$ Asp-Ile-Glu-Lys-Lys-Ile-Ala-Lys-Met-Lys-Ala-Ser-Ser-Val-Phe-Asn-Val-Val-Asn-Ser (DIEKKIAKMEKASSVFNVVNS) [Seq. ID No. 17]; ovalbumin $_{323-336}$ Ile-Ser-Gln-Ala-Val-His-Ala-Ala-His-Ala-Glu-Ile-Asn-Glu [Seq. ID No. 35] and the influenza epitope $_{307-319}$ Pro-Lys-Tyr-Val-Lys-Gln-Asn-Thr-Leu-Lys-Leu-Ala-Thr [Seq. ID No. 18].

In preferred embodiments the CTL inducing peptides of the invention are covalently linked to the T helper peptides. Particularly preferred CTL inducing peptides/T helper conjugates are linked by a spacer molecule. Alternatively, the CTL peptide may be linked to the T helper peptide without a spacer. The spacer is typically comprised of relatively small, neutral molecules, such as amino acids or amino acid mimetics, which are substantially uncharged under physiological conditions and may have linear or branched side chains. The spacers are typically selected from, e.g., Ala, Gly, or other neutral spacers of nonpolar amino acids or neutral polar amino acids. In certain preferred embodiments herein the neutral spacer is Ala. It will be understood that the optionally present spacer need not be comprised of the same residues and thus may be a hetero- or homo-oligomer. Preferred exemplary spacers are homo-oligomers of Ala. When present, the spacer will usually be at least one or two residues, more usually three to six residues. In other embodiments the T helper peptide is conjugated to the CTL peptide, preferably with the T helper peptide positioned at the amino terminus. The peptides may be joined by a neutral linker, such as Ala-Ala-Ala or the like, and preferably further contains a lipid residue such as palmitic acid or the like (as described further below) which is attached to alpha and epsilon amino groups of a Lys residue ((PAM)$_2$Lys), which is attached to the amino terminus of the peptide conjugate, typically via Ser-Ser linkage or the like.

The CTL inducing peptide may be linked to the T helper peptide either directly or via a spacer either at the amino or carboxy terminus of the CTL peptide. The amino terminus of either the CTL inducing peptide or the T helper peptide may acylated. In addition, the CTL peptide/T helper conjugate may be linked to certain alkanoyl (C$_1$–C$_{20}$) lipids via one or more linking residues such as Gly, Gly-Gly, Ser, Ser-Ser as described below.

In an exemplary embodiment described below, a T helper peptide from substantially within HBc$_{128-140}$ (Thr-Pro-Pro-Ala-Tyr-Arg-Pro-Pro-Asn-Ala-Pro-Ile-Leu) [Seq. ID No. 19]), when linked with the CTL peptide (HBc18–27), was shown to induce specific CTL priming of animals in all animals studied, and at levels which were greater than when the CTL peptide and T helper peptide were administered unlinked. When the T helper and CTL HBV peptides were linked by a Ala-Ala-Ala spacer, specific CTL activity greater than induction of specific CTL activity with the linked peptides without spacer. These results suggest enhanced CTL response against cells which display HBV antigens when the peptide containing a CTL epitope is linked via spacer to a peptide containing a HBV T helper epitope is used as the immunogen.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference.

Alternatively, recombinant DNA technology may be employed wherein a nucleotide sequence which encodes a CTL peptide and/or T helper peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, cold Spring Harbor Press, Cold Spring Harbor, New York (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, which disclosures are incorporated herein by reference. Thus, fusion proteins which comprise one or more peptide sequences of the invention can be used to present the HBV cytotoxic T cell determinants. For example, a recombinant HBV surface antigen protein is prepared in which the HBenv amino acid sequence is altered so as to more effectively present epitopes of peptide regions described herein to stimulate a CTL response. By this means a polypeptide is used which incorporates several T cell epitopes.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent HBV infection. As the peptides are used to stimulate cytotoxic T-lymphocyte responses to HBV infected cells, the compositions can be used to treat or prevent acute and/or chronic HBV infection.

For pharmaceutical compositions, the peptides, i.e., the CTL peptide or CTL/T helper peptide, of the invention as described above will be administered to an individual already infected with HBV. Those in the incubation phase or the acute phase of infection can be treated with the immunogenic peptides separately or in conjunction with other treatments, as appropriate. In therapeutic applications, compositions are administered to a patient in an amount sufficient to elicit an effective CTL response to HBV and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 500 μg of peptide for a 70 kg patient, followed by boosting dosages of from about 1.0 μg to about 100 μg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HBV infection or shortly after diagnosis in the case of acute infection, to be followed by boosting doses until at least symptoms are substantially abated and for a period thereafter. In chronic infection, loading doses followed by boosting doses may be required. The elicitation of an effective CTL response to HBV during treatment of acute hepatitis will minimize the possibility of subsequent development of chronic hepatitis, HBV carrier stage, and ensuing hepatocellular carcinoma.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic hepatitis and to stimulate the immune system of carriers to eliminate virus-infected cells. Those with chronic hepatitis can be identified as testing positive for virus from about 3–6 months after infection. As individuals may develop chronic HBV infection because of an inadequate (or absent) CTL response during the acute phase of their infection, it is important to provide an amount of immuno-potentiating peptide in a formulation and mode of administration sufficient to effectively stimulate a cytotoxic T cell response. Thus, for treatment of chronic hepatitis, a representative dose is in the range of about 1.0 μg to about 500 μg, preferably about 5 μg to 100 μg for a 70 kg patient per dose. Administration should continue until at least clinical symptoms or laboratory indicators indicate that the HBV infection has been eliminated or substantially abated and for a period thereafter. Immunizing doses followed by boosting doses at established intervals, e.g., from one to four weeks, may be required, possibly for a prolonged period of time, as necessary to resolve the infection. For the treatment of chronic and carrier HBV infection it may also be desirable to combine the CTL peptides with other peptides or proteins that induce immune response to other HBV antigens, such as HBsAg.

In another embodiment of the invention, chronic active hepatitis is treated using antigenic epitope analogs as antagonists. The analog antagonists bind to the appropriate MHC class I antigen, but prevent CTL activation and proliferation, thereby reducing damage to HBV infected hepatocytes and T cell mediated liver inflammation. The peptide antagonists comprise a CTL epitope peptide which has been modified, e.g., by amino acid substitution, such that the peptide binds effectively to the Class I MHC molecule but its ability to stimulate epitope specific T cells is substantially reduced.

Analog antagonists are identified by making modifications to a peptide which contains at least one HLA class I epitope. In preferred embodiments the peptide to be modified will comprise a class I-restricted CTL epitope. Substitutions or other selected modifications are introduced into the peptide, which peptide analog is then screened for the ability to block the presentation of an unrelated antigen epitope, such as an influenza peptide, to an influenza-specific T cell clone restricted by the same class I molecule. For example, an HLA-A2 restricted CTL peptide as described herein is modified, e.g., by one or more point substitutions, and then tested for the ability to block the presentation of HLA-A2-restricted influenza CTL matrix peptide (e.g., 56–68) to an influenza-specific T cell clone restricted by HLA-A2. Antagonist analogs will inhibit T cell proliferation and/or cytolytic activity when the antigen presenting cell/target cell is exposed to the antagonist peptide after exposure to a stimulatory dose of the antigenic peptide. Antagonist analogs of the invention can be identified for a variety of HBV class I epitopes, including those described in, e.g., U.S. Pat. No. 4,882,145 and Ferrari et al., *J. Clin. Invest.*, supra.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the CTL stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Lipids have been identified as agents capable of priming CTL in vivo against viral antigens. For example, palmitic acid residues can be attached to the alpha and epsilon amino groups of a Lys residue and then linked, e.g., typically via one or more linking residues such as Gly, Gly-Gly-, Ser, Ser-Ser, or the like, to a synthetic peptide which comprises a class I-restricted CTL epitope. As further described herein, the lipidated peptide can then be incorporated into a liposome emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of a class I restricted peptide having T cell determinants, such as those peptides described herein as well as other peptides which have been identified has having such determinants.

As another example of lipid priming of CTL responses, *E. coli* lipoprotein, such as tripalmitoyl-S-glycerylcysteinyl-seryl-serine ($P_3CSS$), can be used to prime virus specific CTL when covalently attached to an appropriate peptide. See, Deres et al., *Nature* 342:561–564 (1989), incorporated herein by reference. Peptides of the invention can be coupled to $P_3CSS$, for example, and the lipopeptide administered to an individual to specifically prime a CTL response to HBV. Further, as the induction of neutralizing antibodies can also be primed with $P_3CSS$ conjugated to a peptide which displays an appropriate epitope, e.g., HBsAg epitopes, the two compositions can be combined to more effectively elicit both humoral and cell-mediated responses to HBV infection. Yet another example of lipid priming of CTL response is achieved by conjugating the CTL/T helper-peptide-conjugate with uncharged fatty acid residues of different chain lengths and degrees of unsaturation, ranging from acetic to stearic acid as well as to negatively charged succinyl residues via the appropriate carboxylic acid anhydrides.

CTL responses to a variety of other antigens may be enhanced by combining a CTL inducing peptide/T helper inducing peptide conjugate with a lipid. The CTL inducing peptides may be selected from target proteins, such as, e.g. renal cell carcinoma, breast cancer, carcinoembryonic antigens, melanoma (MAGE-1) antigens, prostate cancer specific antigen (PSA), hepatitis C antigens, Epstein-Barr virus antigens, HIV-1 and HIV-2 antigens, and papilloma virus antigens, among others. The lipid may be linked to other peptides which present T helper epitopes which are then combined with the lipid. The arrangement of the components of the conjugate comprising the CTL inducing peptide/T helper peptide/lipid can be varied. In one case, the lipid moiety can be linked to the amino terminal end of the CTL inducing peptide, which in turn is linked at its carboxy terminal to the T helper peptide. In another case, the lipid is linked at the amino terminal end of the T helper peptide, which is linked at its carboxy terminal to the CTL inducing peptide. In each case, a spacer molecule can be selectively inserted between the lipid moiety and the CTL or T helper peptide, as well as between the T helper and the CTL inducing peptides. In the case of the spacer between the lipid and the T helper or CTL inducing peptide, a preferred example comprises Lys-Ser-Ser, although other spacers are described herein. An example of a spacer between the T helper and CTL inducing peptides will be Ala-Ala-Ala, as also described in further detail herein. The CTL inducing peptide can be from the HBc or HBs region, or from other CTL inducing antigens as noted above.

The concentration of CTL stimulatory peptides of the invention in the pharmaceutical formulations can vary widely, i.e., from less than about 1%, usually at or at least about 10% to as mush as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Sciences,* 17th ed., Mack Publishing Company, Easton, Pa. (1985), which is incorporated herein by reference.

The peptides of the invention may also be administered via liposomes, which serve to target the peptides to a particular tissue, such as lymphoid tissue, or targeted selectively to HBV infected hepatic cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the CTL stimulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of a CTL stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HBV. Useful carriers are well known in the art, and include, e.g., thyroglobulin, albumins such as human serum albumin, tetanus toxoid, polyamino acids such as poly(D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of CTLs specific for HBV surface and/or nucleocapsid antigen, and the host becomes at least partially immune to HBV infection, or resistant to developing chronic HBV infection.

Vaccine compositions containing the peptides of the invention are administered to a patient susceptible to or otherwise at risk of HBV infection to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 µg to about 500 µg per 70 kilogram patient, more commonly from about 50 µg to about 100 µg mg per 70 kg of body weight. The peptides are administered to individuals of an appropriate HLA type, e.g., for vaccine compositions of peptide $HBenv_{309-328}$, $HBenv_{349-368}$ and $HBc_{91-110}$, these will be administered to HLA-A2 individuals.

In some instances it may be desirable to combine the peptide vaccines of the invention with vaccines which induce neutralizing antibody responses to HBV, particularly to HBV envelope antigens, such as recombinant HBV env-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, European Patent publications EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386, each of which is incorporated herein by reference. The vaccines can be combined and administered concurrently, or as separate preparations.

For therapeutic or immunization purposes, the peptides of the invention can also be expressed by attenuated viral hosts, such as vaccinia or fowlpox. This approach involves the use of vaccinia virus as a vector to express nucleotide sequences that encode the peptides or conjugates of the invention. Upon introduction into an acutely or chronically HBV-infected host or into a non-infected host, the recombinant vaccinia virus expresses the HBs and/or HBc peptide, and thereby elicits a host CTL response to HBV. Vaccinia vectors and methods useful in immunization protocols are described in, e.g., U.S. Pat. No. 4,722,848, incorporated herein by reference. Another vector is BCG (bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

EXAMPLE I

Identification of CTL-Specific HBV Epitopes

A line of transgenic mice which express a mouse-human chimeric class I molecule was used to define HBV core and surface antigen sequences that represent CTL-specific epitopes.

The transgenic mouse line 66 obtained from Scripps Clinic and Research Foundation expresses a chimeric class I molecule composed of the $\alpha 1$ and $\alpha 2$ domains of human HLA-A2.1 antigen and the $\alpha 3$ transmembrane and cytoplasmic domains of $H-2K^b$. The transgenic mice were prepared as generally described in Vitiello et al., *J. Exp. Med.* 173:1007–1015 (1991), which is incorporated herein by reference. When these mice are primed in vivo with the influenza virus, they generate a CTL response that is specific for virtually the same epitopes as those recognized by human influenza-specific CTL. Thus, these transgenic animals can be used to determine HBV epitopes recognized by human T cells.

To define which sequence regions within HBV surface and core proteins represented CTL epitopes, synthetic peptides derived from the two proteins were prepared and tested for their ability to bind to human HLA-A2.1. Binding was determined by the relative capacity of different peptide concentrations to inhibit recognition of A2.1 target cells in the presence of the influenza matrix peptide 57–68 by the CTL line 219, as determined by the inhibition of release of serine esterase from the cells. The 219 line was derived from A2.1 transgenic mice and is specific for the matrix peptide 57–68 in the context of HLA-A2.1.

Briefly, peptides to be assayed for CTL epitopes were dissolved in DMSO at a concentration of 20 mg/ml. Just before the assay, peptides were diluted in RPMI 1640 buffered with 25 μM Hepes and containing 0.05% BSA (assay media). Fifty microliters of a 200 μg/ml, 66 μg/ml, or 22 μg/ml of peptide solution were added to wells of 96 round-bottomed plates containing $4\times10^5$ Jurkat A2.1/$K^b$ cells in a volume of 50 μl of assay media. Plates were incubated for 30 min. at 37° C. Fifty μl of 2.5 μg/ml solution of the index peptide (matrix peptide 57–68 from PR8 influenza virus) were then added to the cells, followed by 50 μl containing $5\times10^4$ line 219 CTL, where the concentration of index peptide used was chosen as that which induced 75% serine esterase release from CTL 219, as determined by titration of the peptide. After 4 hours incubation at 37° C., plates were centrifuged for 5 min. at 1000 RPM, and 20 μl supernatant transferred to flat-bottomed 96-well plates. Esterase activity in the supernatant was measured by adding 180 μl of a reaction mixture consisting of 0.2M TrisHCl pH 8.1, $2.0\times10^{-4}$ N-benzyloxycarbonyl-L-Lysine thiobenzyl ester (BLT) and $2.2\times10^{-4}$ M dithiobis (nitrobenzoic acid). Plates were incubated for 1 hour at 37° C. and absorbance read at 412 nm. Percent inhibition was calculated by the following formula:

$$\% \text{ inhibition} = 100 - \frac{A_{412}(\text{test} + \text{index}) \text{ peptide} - A_{412} \text{ test peptide alone}}{A_{412} \text{ index peptide} - A_{412} \text{ no peptide}} \times 100$$

Those peptides which bound to A2.1 and caused more than 24% inhibition of serine esterase release by the cells were assayed in vitro for the ability to restimulate a CTL response from splenocytes derived from HBV primed A2.1 transgenic mice. (Sette, A. et al., *J. Immunol.* 147:3893 (1991). HBV priming was performed by injecting A2.1 spleen cells "loaded" with HBV virus as described by Carbone and Bevan, *J. Exp. Med.* 171:377–387 (1990).

Briefly, red blood cell depleted splenocytes were suspended in 0.4 ml of a solution composed of 200 μl of HBV purified virus and 200 μl of a 2×hypertonic solution (0.5 M sucrose, 10% w/v polyethylene glycol 1000, 10 mM Hepes, pH 7.2, in RPMI 1640 medium), for 10 min. at 37° C. The cell suspension was then rapidly diluted in prewarmed hypotonic media (60% HBSS and 40% water), incubated for 2 min. at 37° C., pelleted, washed twice in HBSS and irradiated (1,000 rad.). Mice were then injected with $5.0\times10^6$ loaded cells in a volume of 200 μl. Mice were boosted with HBV-loaded spleen cells 10 days later.

After about 2 weeks, spleen cells from primed mice ($5\times10^6$ cells/well in 24 well plates) were cultured with 4 different mixtures of syngeneic irradiated (3000 rads) LPS blasts ($2\times10^6$ cells/well) that had been independently coated with 13 different peptides. Coating was achieved by incubating aliquots of $25\times10^6$ LPS blasts in tubes each with 100 μg of one of the 13 HBV synthetic peptides in one mL for 1–2 hrs at 37° C.; the contents of the different tubes were then pooled to give 4 mixtures.

| Mixture No. | Peptide No. | Peptide Location |
|---|---|---|
| 1 | 800.04 | HBenv47–63 |
|  | 802.01 | HBc11–27 |
|  | 802.06 | HBc162–176 |
| 2 | 801.02 | HBenv141–157 |
|  | 799.02 | HBenv194–213 |
|  | 802.03 | HBc91–110 |
| 3 | 799.09 | HBenv329–348 |
|  | 799.10 | HBenv349–368 |
|  | 802.04 | HBc111–125 |
| 4 | 799.04 | HBenv234–253 |
|  | 799.05 | HBenv246–265 |
|  | 799.08 | HBenv309–328 |
|  | 800.05 | HBenv63–77 |

The mixture of cells was washed once, diluted at the required concentration and plated. The medium used for the cultures was RPMI 1640 supplemented with 10% FCS, 50 μg/ml gentamicin, 2 mM glutamine and $5\times10^{-5}$ M 2-mercaptoethanol (R10). After nine days, effector cells were assayed for cytotoxicity against Jurkat $A_2/k^b$ target cells in the presence of different peptide mixtures corresponding to those used in the cultures. The results obtained are shown in FIG. 1 panels, A through D. The effector cells ($0.2\times10^6$ cells/well) obtained from these cultures were restimulated with irradiated (20,000 rads), peptide-coated Jurkat A2/$K^b$ cells ($0.2\times10^6$ cells/well) in the presence of $3\times10^6$ feeder cells/well (C57BL/6 irradiated spleen cells) in R10 supplemented with 5%-rat ConA supernatant. After 6 days, these effector cells were assayed for cytotoxicity against $^{51}$Cr labeled Jurkat $A_2/K^b$ target cells in the presence of the 13 individual peptides. Peptides that induced CTL lysis of Jurkat $A_2/K^b$ target cells above background (FIG. 1, panels E through H) i.e., HBenv 47–63, HBc 11–27 (panel E) HBenv 141–157, HBenv 194–213, HBc 91–110 (panel F), HBenv 329–348 and 349–368 (panel G) and HBenv 309–328 (panel H) were independently used to restimulate the effector cells generated with the peptide mixtures. After 6 d in culture, the effector cells were tested for cytotoxicity against $^{51}$Cr Jurkat $A_2/K^b$ cells in the presence of the peptide used for the restimulation (FIG. 1). The set of experiments, outlined in this example allow us to determine that HBV peptides HBc 11–27 (FIG. 1 panels A,E; FIG. 2 panel J) HBc 91–110 (FIG. 1 panels B,F; FIG. 2 panel M), HBenv 329–348 (FIG. 1 panels C,G; FIG. 2 panel N) HBenv 349–368 (FIG. 1 panels C,G; FIG. 2 panel O) and HBenv 309–328 (FIG. 1 panels D,H; FIG. 2 panel P) clearly represent CTL epitopes.

EXAMPLE II

Induction of A2.1-restricted CTL by Subcutaneous Priming with Purified HBV in Incomplete Freund's Adjuvant (IFA)

Injection of ovalbumin (OVA) in IFA subcutaneously induces an ovalbumin-specific CTL response in mice, while injection of OVA either i.v. or i.p. generally does not lead to the generation of CTL. This technique was used to induce HBV-specific CTL in A2.1 transgenic mice.

Priming and In Vitro Restimulation: A2.1/$K^b$ transgenic mice were injected with 100 microliters of an emulsion of purified HBV virus in incomplete Freund's adjuvant (IFA). This emulsion was prepared by mixing purified HBV (1 mg protein/ml) diluted 1:5 in HBSS with an equal volume of IFA. Seven days after priming, splenocytes (5×10⁶ cells/well in a 24 well plate) obtained from these animals were restimulated with syngeneic irradiated LPS blasts (2×10⁶/well) coated with each of the following peptides:

| 799.09 | HBenv 329–348 | 802.03 | HBc 91–110 |
| 875.20 | HBenv 335–343 | 883.02 | HBc 92–101 |
| 875.21 | HBenv 338–347 | 883.03 | HBc 93–102 |
| 799.10 | HBenv 349–368 | 875.15 | HBc 18–27 |
| 884.01 | HBenv 348–357 | 875.18 | HBc 107–115 |
| 884.02 | HBenv 349–358 | 875.19 | HBc 139–148 |

These peptides were chosen because: 1) They had been defined as containing CTL epitopes in Example I (peptides 799.10, 799.09, 802.03); 2) they represent truncations of peptides defined in Example I that are recognized by the CTL raised against the larger epitopes (i.e., peptides 875.15, 884.02, 883.02, 883.03); or 3) they contain the A2.1 binding motif as described by Falk et al. (*Nature* 351:290–296 (1991)), i.e., leucine or methionine in position 2, and either leucine or valine in position 9 or valine in position 10, (i.e., peptides 884.01, 875.20, 875.21, 875.18 and 875.19). Coating was achieved by incubating 50 μg of each individual peptide with 12×10⁶ LPS blasts in a volume of 0.4 ml of RPMI medium supplemented with 10% FCS for 1 h at 37° C. The cells were washed once. After 6 days, effector cells were assayed for cytotoxicity against ⁵¹Cr labelled Jurkat A2/K$^b$ cells in the presence of the appropriate peptides. The results are shown in FIG. 3.

These effector cells (0.2×10⁶ cells/well) were restimulated at weekly intervals. For the first restimulation, peptide-coated LPS blasts were used, followed by peptide-coated Jurkat A2.1/K$^b$ cells. Six days after restimulation, effector cells were assayed for cytotoxicity against ⁵¹Cr labelled Jurkat A2/K$^b$ target cells in the presence of the appropriate peptides. The results obtained are shown in FIG. 4.

Peptides clearly able to induce in vitro CTL from splenocytes of HBV-primed mice are FIGS. 3 and 4, panel A: HBc 18–27; FIGS. 3 and 4, panel B: HBenv 349–368; FIGS. 3 and 4, panel D: HBenv 349–358; FIGS. 3 and 4, panel F: HBenv 329–348; FIGS. 3 and 4, panel I: HBc 91–110; FIGS. 3 and 4, panel J: HBc 92–102; and FIGS. 3 and 4, panel K: HBc 93–102. Truncation peptides recognized by CTL raised against the larger peptide and as such should contain at least part of a CTL epitope are: FIGS. 3F, 4F: HBenv 335–343 and HBenv 338–347.

EXAMPLE III

Synthesis of Peptides

Peptides were synthesized on an Applied Biosystems (Foster City, Calif.) 430A peptides synthesizer using Fmoc protected amino acids and 2-(1H-Benzotriazol-1-yl)-1,1,3,3-tetramethyluronium hexafluorophosphate (HBTU) esters for amino acid activation. Each amino acid were routinely triple coupled. Fmoc protected amino acids and Hydroxybenzotriazole were purchased from Burdick and Jackson. HBTU was purchased from Richelieu Biotechnologies (St-Hyacinthe, Canada). Piperidine and trifluoroacetic acid, acetic anhydride, and ethanedithiol were purchased from Sigma Chemical Corporation.

a. Peptide Phe-Leu-Pro-Ser-Asp-Phe-Phe-Pro-Ser-Val-OH [Seq. ID No. 23]

L-Valine coupled to Sasrin® resin (Bachem Biosciences) was loaded into the peptide synthesis reaction vessel and washed one time with N-methylpyrolidone (NMP). The following operations were then sequentially performed:

1. The Fmoc protecting group was removed by treatment of the resin bound amino acid with 25% piperidine in NMP.
2. The resin was washed 5 times with NMP.
3. A mixture containing Fmoc-serine, diisopropylethylamine, HBTU and NMP was added to the reaction vessel and allowed to react for 30 minutes, under vortex agitation.
4. The solvent was drained, and the resin was washed three times with NMP.

Steps (3) and (4) were repeated two more times.

The resin was washed four more times with NMP. Steps 1–6 were repeated for each amino acid of the peptide. Following the final coupling cycle, the resin-bound peptide was deproteced by reaction with 25% piperidine in NMP, washed 7 times with NMP, and washed 2 times with dichloromethane. The resin was dried in vacuo for 24 hours. The peptide was cleaved from the Sasrin® resin by treatment with trifluoroacetic acid containing 2.5% ethanedithiol and 5% water. The polystyrene resin was separated from the trifluoroacetic acid solution by filtration. Trifluoroacetic acid was removed by evaporation in vacuo. The crude peptide was triturated with diethylether and dissolved in water. The water was removed by lyophilization. The peptide was then purified by reverse phase HPLC on a C₈ column (VYDAC) using a gradient of acetonitrile, water, each containing 0.1% TFA as modifier.

b. Peptide (Pal)₂-Lys-Ser-Ser-Phe-Leu-Pro-Ser-Asp-Phe-Phe-Pro-Ser-Val-OH [Seq. ID No. 24]

The resin bound peptide described in section a was extended by the addition of two serine residues according to the above described procedure. The following operations were then performed:

1. The Fmoc protecting group was removed by treatment of the resin bound amino acid with 25% piperidine in NMP.
2. The resin was washed 5 times with NMP.
3. Bis-Fmoc-Lysine was converted to the corresponding symmetrical anhydride by treatment with diisopropylcarbodiimide in NMP. The resin bound peptide was allowed to react with the resulting anhydride.
4. The resin was washed 5 times with NMP.
5. The Fmoc protecting group was removed by treatment of the resin bound amino acid with 25% piperidine in NMP.
6. Palmitic acid was reacted with hydroxybenzotriazole and diisopropylcarbodiimide in NMP. The resin bound peptide was allowed to react with the resulting solution.
7. The resin was washed 5 times with NMP.

Finally, the peptide was cleaved from the resin as described above.

c. Peptide Gln-Tyr-Ile-Lys-Ala-Asn-Ser-Lys-Phe-Ile-Gly-Ile-Thr-Glu-Phe-Leu-Pro-Ser-Asp-Phe-Phe-Pro-Ser-Val-OH [Seq. ID No. 25].

The resin bound peptide described in section a was chain extended by the addition of Glu, Thr, Ile, Gly, Ile, Phe, Lys, Ser, Asn, Ala, Lys, Ile, Tyr, and Gln residues, according to the procedure described in Section a. Cleavage and purification were performed as described above.

d. Peptide Gln-Tyr-Ile-Lys-Ala-Asn-Ser-Lys-Phe-Ile-Gly-Ile-Thr-Glu-Ala-Ala-Ala-Phe-Leu-Pro-Ser-Asp-Phe-Phe-Pro-Ser-Val-OH [Seq. ID No. 26].

The resin bound peptide described in section a was chain extended by the sequential addition of Ala, Ala, Ala, Glu, Thr, Ile, Gly, Ile, Phe, Lys, Ser, Asn, Ala, Lys, Ile, Tyr, and Gln residues, according to the procedure described in section a. Cleavage and purification were performed as described above.

e. Peptide Ac-Gln-Tyr-Ile-Lys-Ala-Asn-Ser-Lys-Phe-Ile-Gly-Ile-Thr-Glu-Ala-Ala-Ala-Phe-Leu-Pro-Ser-Asp-Phe-Phe-Pro-Ser-Val-OH [Seq. ID No. 27].

The resin bound peptide described in Section d was acetylated by reaction with acetic anhydride in NMP. Cleavage and purification were performed as described above.

EXAMPLE IV

Induction of CTL By Combining CTL and T-Helper Epitopes

This example describes experiments which define the relative in vivo HBV-specific CTL priming efficiency of peptides expressing HBV CTL epitopes alone, CTL epitopes mixed with peptides containing T helper epitopes or CTL epitopes physically linked to T helper epitopes.

Figure 5:
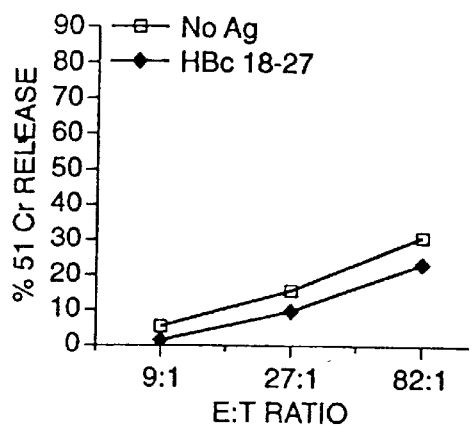
FIG. 5 illustrates that no HBc18-27-specific CTL response is detected in mice primed with the HBc 875.23 T helper epitope alone. Animals were primed subcutaneously with 100 μg of 875.23 (T helper epitope) in Complete Freund's Adjuvant (CFA) followed 9 days later (subcutaneously) with IFA alone. Splenocytes were removed 3 weeks later, cultured for 6 days in the presence of LPS-blasts that had been incubated with the CTL epitope (875.15), 100 μg for 2 hrs before being washed and added to the culture as a source of antigen presenting cells. The presence of HBc 18-27 (875.15)-specific CTL was determined using a standard 6 hr $^{15}$Cr release assay with Jurkat A2.1/K$^b$ cells as targets.
Figure 6:
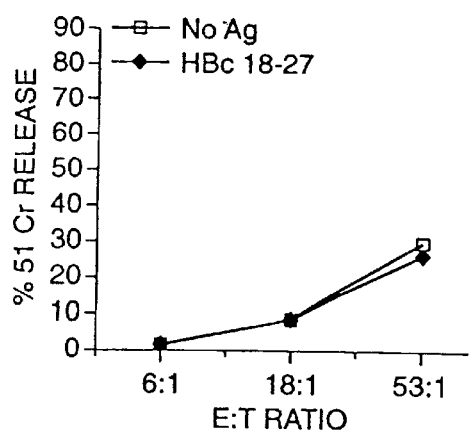
FIG. 6 illustrates that no HBc 18-27-specific CTL response was detected when mice were primed with HBc18-27 (875.15) in IFA. Experimental protocol was similar to that described in FIG. 5, except that mice received 100 μg of peptide 875.15 subcutaneously in IFA rather than IFA alone for in vivo CTL priming.
Figure 7:
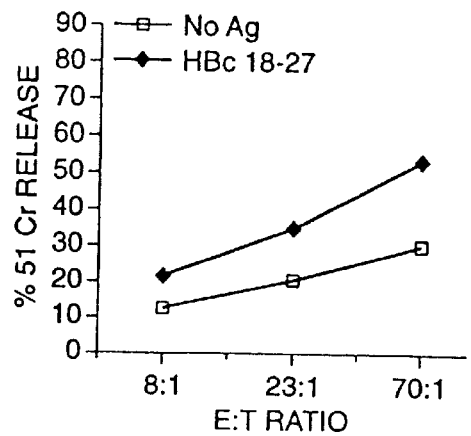
FIG. 7 illustrates that HBc18-27-specific CTL response was detected in 50% of the mice primed with HBc T helper peptide (875.23) mixed with HBc CTL inducing peptide (875.15) at a 1 to 1 ratio. The experimental protocol was similar to that described in FIGS. 5 and 6.
Figure 8:
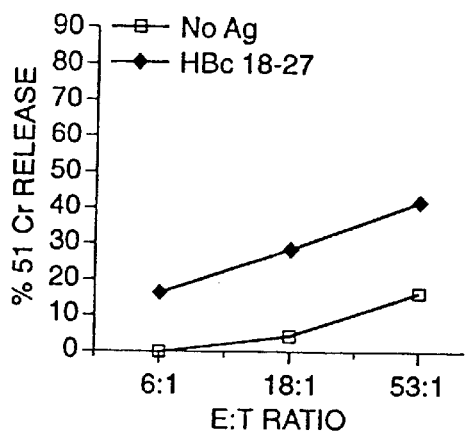
FIG. 8 illustrates the HBc-specific (875.15) CTL activity was detected in mice primed with peptide 902.01 in which the HBc T helper and CTL inducing peptide were linked via a peptide bond. Experimental protocol was similar to that in FIGS. 5 and 6.
Figure 9:
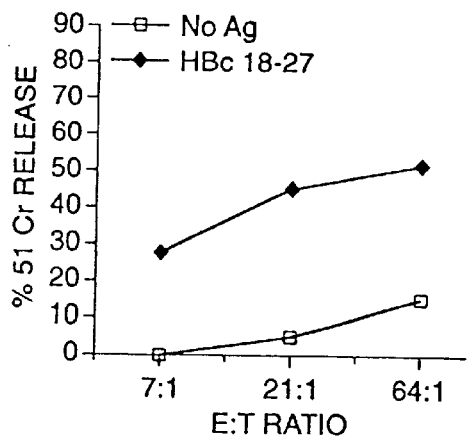
FIG. 9 illustrates that the greatest HBc18-27 (875.15)-specific CTL activity was detected in mice primed with peptide 902.02 in which the HBc T helper and CTL epitopes were linked via peptide bonds using an exemplary spacer such as alanine-alanine-alanine. Protocol was similar to that in FIGS. 5 and 6.
Figure 10A:
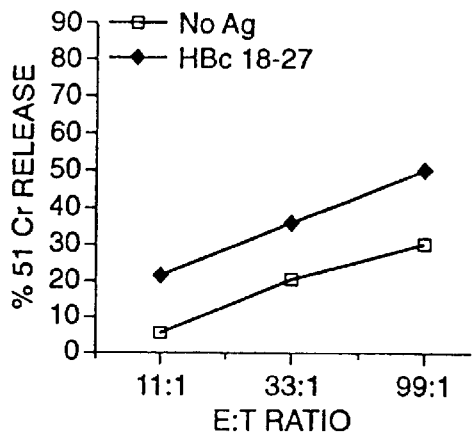
FIG. 10 illustrates that previous priming of helper T cells was not required for in vivo priming of HBc 18-27-specific CTL responses using peptide 902.01 and 902.02. CTL response is shown from animals primed subcutaneously with peptide 902.01 (FIG. 10A) or (902.02 ) (FIG. 10B) alone without the previous priming with peptide 875.23 in CFA.
Figure 10B:
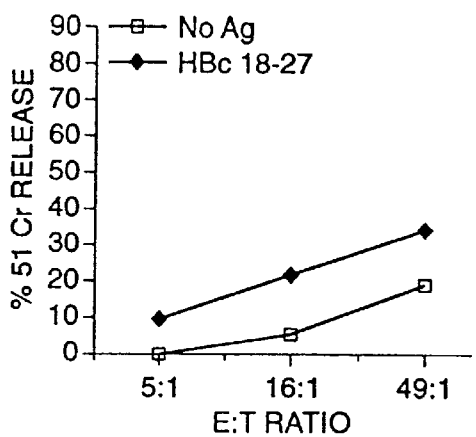

Transgenic mice (HLA-A2.1/$K^b$) were primed subcutaneously (base of tail) with 100 µg of peptide 875.23 ($Ia^b$-restricted helper epitope HBc 128–140 TPPAYRPPNAPIL) in complete Freund's adjuvant (CFA). Nine days later each of the following peptides were injected subcutaneously into two unprimed and two helper-primed mice, 100 µg/mouse in incomplete Freund's adjuvant (IFA).

of specific CTL priming (FIG. 8), the magnitude of which was greater than that detected when the epitopes were administered non-linked (FIG. 7). Quite unexpectedly, as shown in FIG. 9, it was found that linking the T helper and CTL epitopes via an alanine-alanine-alanine spacer (i.e.,, T helper-AAA-CTL) resulted in the induction of specific CTL activity greater than that detected by linking the T helper and CTL determinants alone. Priming with the T helper peptide or CTL peptide alone did not induce HBc-specific CTL (FIGS. 5 and 6). Also, prior immunization of animals to induce T helper-specific immunity did not appear to be essential for priming for CTL using either the T helper and CTL mixture or the T helper-CTL conjugate, since immunization was detected when naive animals were primed with the appropriate conjugate (FIGS. 10A and B).

EXAMPLE V

Induction of A2.1-Restricted CTL-Specific for $HBenv_{360-368}$

Figure 11:
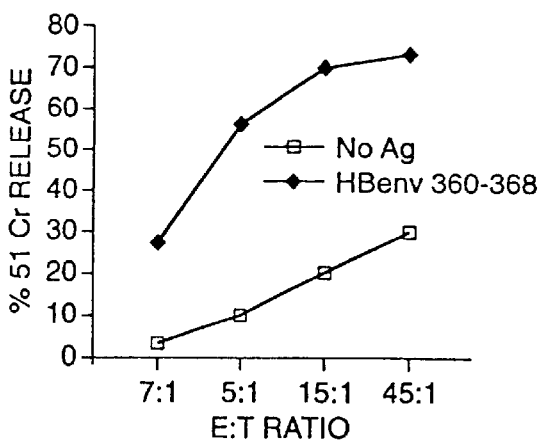
FIG. 11 illustrates the induction of HBenv$_{360-368}$ specific CTL response. A2.K$^b$ transgenic mice were injected with 100 microliters of an emulsion (IFA) of 100 mg HBenv360-368 and 100 mg HBc128-140. Three weeks later, splenocytes were restimulated with syngeneic LPS blasts coated with peptide HBenv360-368. Effector cells were assayed for cytotoxicity against $^{51}$Cr labeled Jurkat A2/K$^b$ target cells in the presence or absence of HBenv 360-368.
Figure 12:
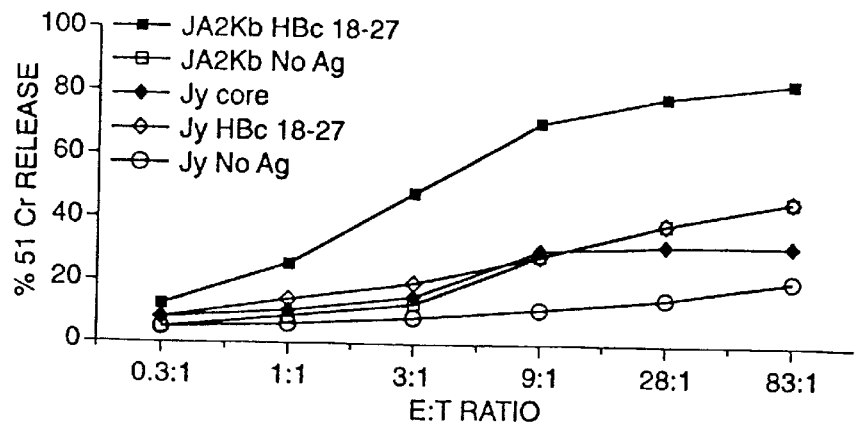
FIG. 12 illustrates the induction of a CTL response specific for HBc 18-27 by priming with a peptide containing HBc 18-27 linked to tetanus toxoid 830-843 (human helper T cell epitope). Effector cells wee assayed against 51Cr labeled Jurkat A2-1/Kb target cells in the present or absence of HBc 18-27; Jy target cells in the presence or absence of HBc 18-27 and Jy cells that had been transfected with HBV core.

A2/$K^b$ transgenic mice were injected with 100 microliters of an emulsion of 100 µg $HBenv_{360-368}$ and 100 µg $HBc_{128-140}$ helper epitope in incomplete Freund's adjuvant (IFA). (This emulsion was prepared by mixing 500 µg of both peptides in PBS with an equal volume of IFA.) Twenty-one days after priming, splenocytes ($5\times10^6$ cells/well in a 24-well plate) obtained from these animals were restimulated with syngeneic LPS blasts ($2\times10^6$/well) coated with the peptide $HBenv_{360-368}$. These effector cells ($0.2\times10^6$/well) were restimulated at weekly intervals. For the first and second restimulations, $HBenv_{360-368}$ coated LPS blasts were used, followed by $HBenv_{360-368}$ coated Jurkat A2.1/$K^b$ cells. Six days after restimulation, effector cells were assayed for cytotoxicity against $^{51}Cr$ labelled Jurkat A2/$K^b$ target cells in the presence and absence of $HBenv_{360-368}$ (see FIG. 11).

| Peptide | T Helper (HBc 128–140) | CTL (HBc 18–27) | Seq. ID |
|---|---|---|---|
| 1. 875.23 | TPPAYRPPNAPIL | | 19 |
| 2. 875.15 | | FLPSDFFPSV | 23 |
| 3. 875.23 + 875.15 | TPPAYRPPNAPIL + | FLPSDFFPSV | 20 |
| 4. 902.01 = | TPPAYRPPNAPILFLPSDFFPSV-NH$_2$ | | 20 |
| 5. 902.02 | TPPAYRPPNAPILAAAFLPSDFFPSV-NH$_2$ | | 21 |
| 6. No peptide | | | |

Three weeks after priming with the CTL epitope, splenocytes were in vitro restimulated with LPS blasts coated with HBc 18–27 (coating was achieved by incubating $30\times10^6$ LPS blasts with 100 µg of HBc18–27 in one ml of medium; after 1–2 hr at 37° C., the cells were washed). After 6 days, effector cells were assayed for lytic activity against $^{51}Cr$ labelled Jurkat $A_2/K^b$ target cells in the presence or absence of HBc18–27.

The results showed that in 50% of the animals studied in which the T helper and CTL epitope peptides were simply mixed (i.e., not linked) and administered in an immunizing dose, induction of some detectable antigen-specific CTL activity above the level of background killing was seen. An example of the response detected is shown in FIG. 7. Surprisingly, when animals were primed with the T helper epitope linked to the CTL epitope, 100% showed evidence

EXAMPLE VI

Testing of Linked Tetanus Toxoid T Helper and HBc Cytotoxic T Cell Epitopes for In Vivo Priming Transgenic mice (HLA-A2-1/kb) were primed subcutaneously (base of the tail) with 200 mg (0.07 mM) of peptide 934.02 [Seq. ID No. 36].

| Peptide | Tetanus Toxoid 830–843 T Helper Epitope | Linker | HBV core 18–27 CTL Epitope |
|---|---|---|---|
| 934.02 | AC-QYIKANSKFIGITE | AAA | FLPSDFFPSV |

| Number | Seq. ID | Peptide pt Peptides | Dose μM/mouse | Formulation |
|---|---|---|---|---|
| 932.01 | 37 | CTL (Flu NP 147–155) TYQRTRALV | 0.1, 0.01 | Saline, Alum, IFA |
| 932.07 | 38 | (PAM)$_2$KSS-CTL (PAM)$_2$KSSTYQRTRALV | 0.1, 0.01 | Saline, Alum, IFA |
| 932.01 +577.01 | 39 | CTL + T helper (OVA 323–336) TYQRTRALV-ISQAVHAAHAEINE | 0.1, 0.01 ea. | Saline, Alum, IFA |
| 932.07 +577.01 | 40 | (PAM)$_2$KSS-CTL + T helper (PAM)$_2$KSSTYQRTRALV-ISQAVHAAHAEINE | .1, 0.01 | Saline, Alum, IFA |
| 932.02 | 41 | T helper-CTL ISQAVHAAHAEINE-TYQRTRALV | 0.1, 0.01 | Saline, Alum, IFA |
| 932.04 | 42 | (PAM)$_2$KSS-T helper-CTL (PAM)$_2$KSSISQAVHAAHAEINE-TYQRTRALV | 0.1, 0.01 | Saline, Alum, IFA |
| 932.03 | 43 | T helper-AAA-CTL ISQAVHAAHAEINE-AAA-TYQRTRALV | 0.1, 0.01 | Saline, Alum, IFA |
| 932.05 | 44 | (PAM)$_2$KSS-T helper-AAA-CTL (PAM)$_2$KSS-ISQAVHAAHAEINE-AAA-TYQRTRALV | 0.1, 0.01 | Saline, Alum, IFA |

Three weeks after immunization splenocytes were removed and stimulated in vitro with the flu 147–155 peptide. CTL activity was assayed one week later using $^{51}$Cr-labeled B10.D2 fibroblasts as targets. Target cells were tested in the absence of antigen, in the presence of Flu 147–155 peptide or following infection with influenza PR8 virus. Representative results obtained from one of four independently run experiments are summarized in Table I.

Table I

CTL Immunogenicity of Various Modifications and Formulations of PR8-NP 148–155

| | Formulation | | | | | |
|---|---|---|---|---|---|---|
| | Saline | | Alum | | IFA | |
| Peptide | 0.01$^a$ | 0.1 | 0.01 | 0.1 | 0.01 | 0.1 |
| 932.01 | –$^b$ | – | – | – | + | +++ |
| 932.07 | ++ | + | – | – | – | – |
| 932.01 + 577.01 | – | ++ | – | – | +++ | ++ |
| 932.07 + 577.01 | + | – | – | – | – | ± |
| 932.02 | – | – | – | +++ | +++ | +++ |
| 932.04 | +++ | +++ | +++ | +++ | +++ | +++ |
| 932.03 | – | – | – | ± | +++ | ++ |
| 932.05 | +++ | +++ | +++ | +++ | +++ | +++ |

$^a$= Dose (μM/mouse)
$^b$= CTL immunogenicity of various modifications and formulations of NP 148–155 (nucleoprotein of PR8 influenza virus). Each symbol represents the result obtained from spleen cells derived from a single Balb/c mouse and reflects the effector to target ratio (E:T) required to induce 40% antigen specific lysis of $^{51}$Cr labeled B10D2 target cells in the presence of ND$_{148-155}$ peptide; +++ E:T below 10:1; ++ E + T between 10 + 1 and 30:1; + E:T greater than 30:1; – not achieved at any E:T tested.

The constructs (PAM$_2$KSS-T helper-CTL and (PAM)$_2$KSS-T helper-AAA-CTL were superior when injected in saline or Alum compared to all of the other combinations. The peptides T helper–CTL and T helper-AAA-CTL were superior to mixing the T helper+CTL (i.e., non-linked) and worked well in IFA, but not well in saline or Alum. Thus, for vaccine development, linking the (PAM)$_2$KSS to a T helper peptide which is linked to the CTL peptide appears to be advantageous for inducing CTL immunity.

EXAMPLE VIII

Definition of the Minimal Optimal Sequence with the CTL Peptide Epitope 799.09

Figure 13A:
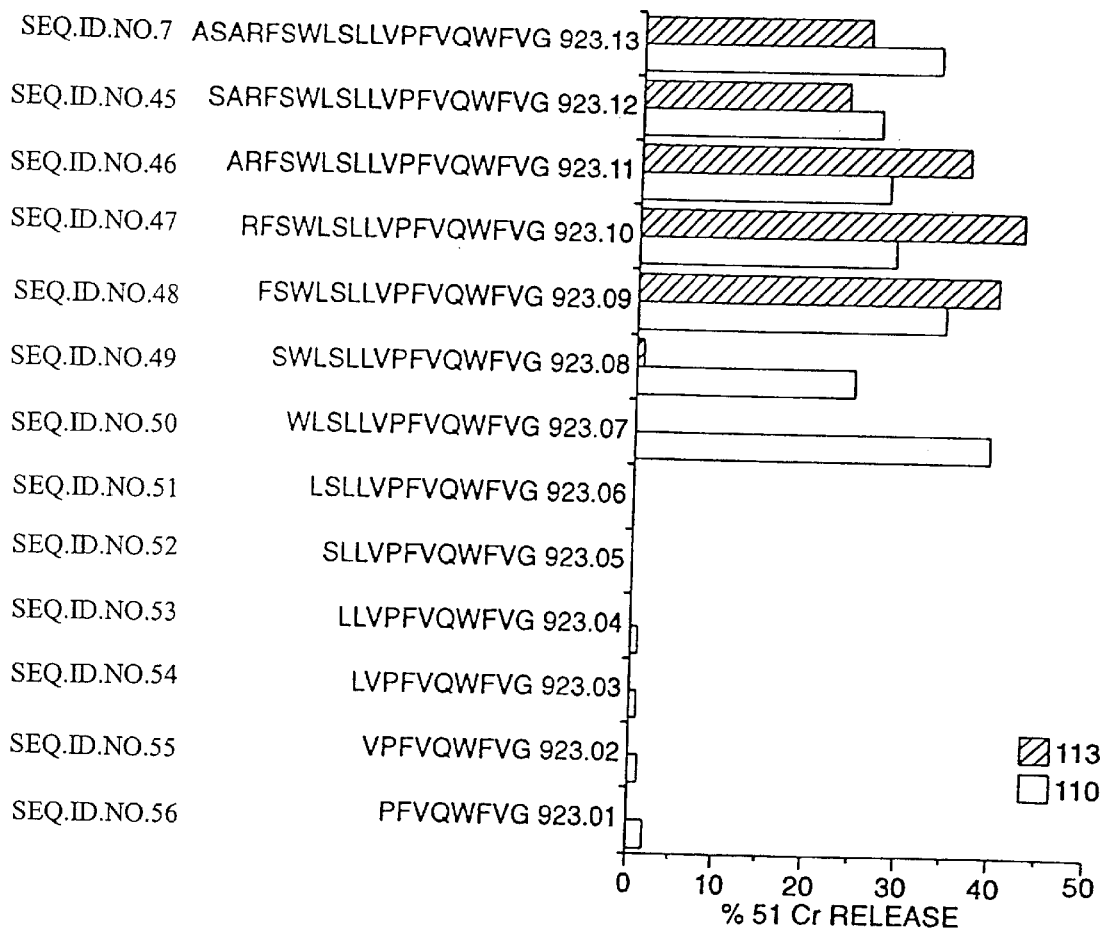
FIGS. 13A and B collectively illustrates the minimal sequence for CTL recognition within HBV env 329-348 peptide (799.09). CTL lines 110 and 113 were derived from splenocytes obtained from A2Kb transgenic mice primed subcutaneously with HBV virus in IFA and in vitro activated with 799.09 coated stimulator cells. 799.09 specific CTL lines 110 and 113 were assayed for lytic activity in a 6 hr 51Cr release assay using JA2Kb cells as targets in the presence of 799.09 peptide truncations (FIG. 13A=799.09 N-terminus truncations.
Figure 13B:
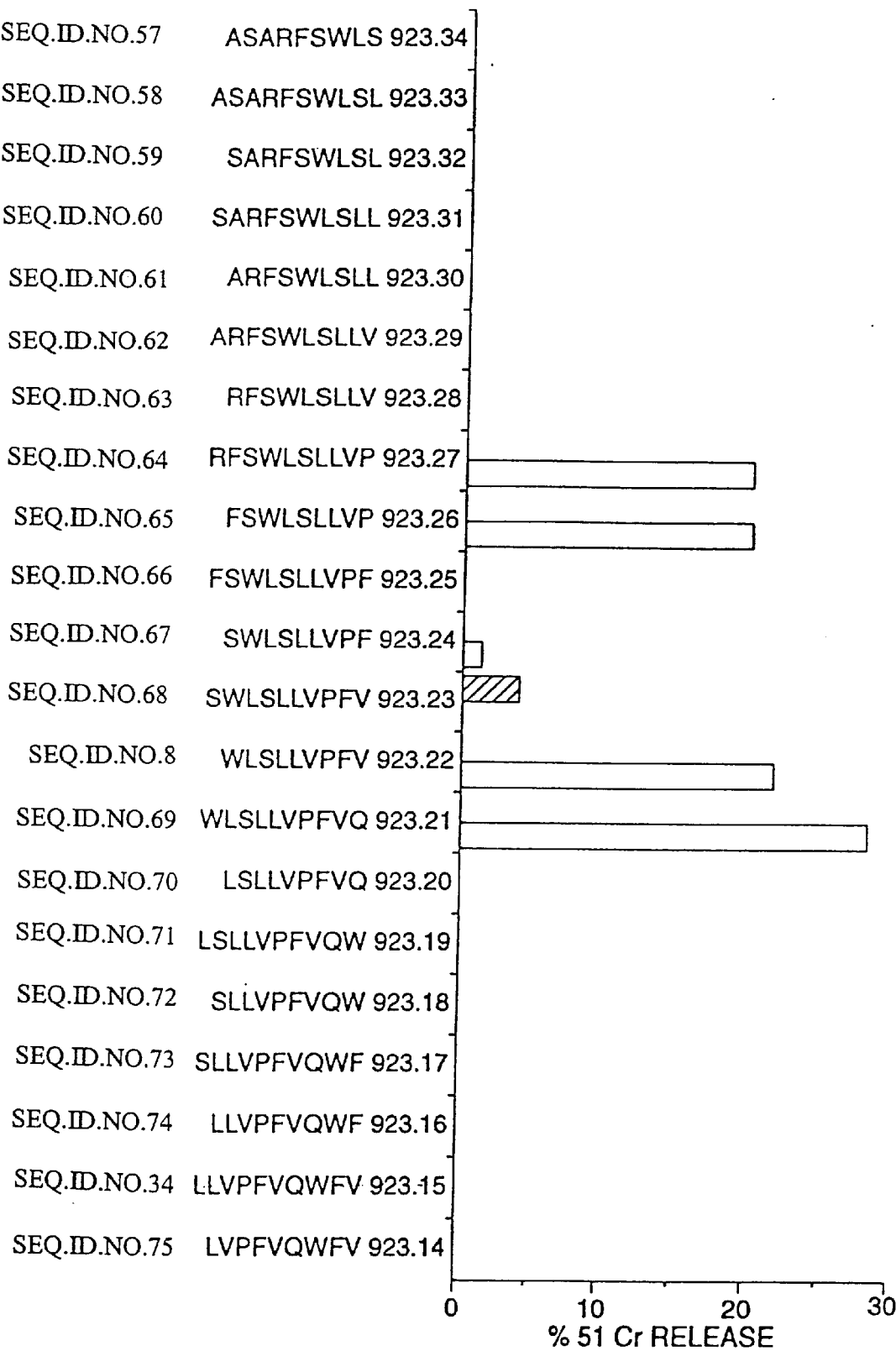
FIG. 13B=799.09 overlapping 9mers and 10 mers).

Transgenic mice (A2-1/Kb) were primed with HBV virus in IFA substantially as described in Example II. Seven days after priming, splenocytes obtained from these animals were restimulated with syngeneic irradiated LPS blasts coated with peptide 799.09 (as described in Example I). After 6 cycles of restimulation with 799.09 coated cells (as described in Example II) the effector cells were cloned by limiting dilution using syngeneic irradiated LPS blasts coated with peptide 799.09 (0.2×10$^6$ cells/well of a 96 well plate) and media supplemented with 10% rat Con A supernatant. Two CTL lines were obtained, line 110 and 113 that killed JA2Kb target cells coated with peptide 799.09. These lines were tested on a panel of 799.09 N-terminus truncated peptides and overlapping 9mers and 10mers covering the entire 799.09 sequence. As shown in FIG. 13 panel A the minimal N-terminus truncated peptide recognized by line 113 and 110 were respectively peptides HBV env. 333–348 (923-09) and 335–348 (923.07). FIG. 13 panel B shows that none of the 9mers or 10mers were recognized by line 113 implicating a longer peptide as the minimal sequence required for recognition by this CTL line. The minimal sequence recognized by line 110 is represented by peptides HBV env. 333–341 (923.26) and HBV env 335–343 (923.22) indicating that possibly two distinct but overlapping peptides can serve as antigenic determinants for 799.09 specific CTL.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An immunogenically effective composition comprising:
   (i) a first peptide comprising an epitope, wherein the first peptide binds to an MHC class I molecule to form an epitope-MHC complex recognized by a cytotoxic T cell;
   (ii) a second peptide comprising an epitope, wherein the second peptide binds to an MHC class II molecule to form an epitope-MHC complex recognized by a helper T cell,
   wherein the first peptide and/or the second peptide is linked to a lipid and further wherein the first peptide or the second peptide are covalently linked or are unlinked; and
   (iii) a physiologically acceptable carrier,
   wherein the epitope comprised in said first peptide comprises a hepatitis B virus epitope.

2. The composition of claim 1, wherein the second peptide is covalently linked to the first peptide.

3. The composition of claim 1, wherein the second peptide is not linked to the first peptide.

4. The composition of claim 3, wherein the lipid is linked to the N-terminus of the second peptide.

5. The composition of claim 1, wherein the second peptide is linked to the lipid.

6. The composition of claim 5, wherein the second peptide is linked to the lipid by a spacer.

7. The composition of claim 5, wherein the spacer molecule is Lys-Ser-Ser.

8. The composition of claim 7, wherein the second peptide is linked to the lipid by a spacer.

9. The composition of claim 5, wherein the lipid comprises palmitic acid attached to epsilon and alpha amino groups of a Lys residue, wherein the Lys is linked to the amino terminus of the second immunogenic peptide by means of a linker.

10. The composition of claim 1, wherein the second peptide is linked at its C-terminal end to the first peptide.

11. The composition of claim 1, wherein the first peptide is linked to the second peptide by a spacer molecule.

12. The composition of claim 11, wherein the spacer molecule between the first peptide and the second peptide is Ala-Ala-Ala.

13. The composition of claim 1, wherein the hepatitis B virus epitope is a hepatitis B core epitope or a hepatitis B envelope epitope.

14. The composition of claim 13, wherein the hepatitis B core epitope is HBc18–27.

15. The composition of claim 1, wherein the first peptide and/or the second peptide are each from six to thirty amino acid residues in length.

16. The composition of claim 1, wherein the first and/or the second peptide comprises a plurality of epitopic units.

17. The composition of claim 1, wherein the physiologically acceptable carrier is physiologic saline or a liposome.

18. The composition of claim 1, comprising an adjuvant.

19. The composition of claim 18, wherein the adjuvant is incomplete Freund's adjuvant, alum, or aluminum hydroxide.

20. The composition of claim 1, wherein the lipid comprises a linear alkyl chain of 6–22 carbons.

21. The composition of claim 20, wherein the lipid comprises a linear alkyl chain of 16 chains.

22. The composition of claim 1, wherein the composition comprises a peptide selected from the group comprising SEQ. ID. NO:1, SEQ. ID. NO:2, SEQ. ID. NO:3, SEQ. ID. NO:4, SEQ. ID. NO:5, SEQ. ID. NO:6, SEQ. ID. NO:7, SEQ. ID. NO:8, SEQ. ID. NO:9, SEQ. ID. NO:22, SEQ. ID. NO:24, SEQ. ID. NO:25, SEQ. ID. NO:26, SEQ. ID. NO:27, SEQ. ID. NO:28, SEQ. ID. NO:29, SEQ. ID. NO:30, SEQ. ID. NO:31, SEQ. ID. NO:32, SEQ. ID. NO:33, SEQ. ID. NO:34, SEQ. ID. NO:37, SEQ. ID. NO:38, SEQ. ID. NO:39, SEQ. ID. NO:40, SEQ. ID. NO:41, SEQ. ID. NO:42, SEQ. ID. NO:43, and SEQ. ID. NO:44.

* * * * *